(12) United States Patent
Seip et al.

(10) Patent No.: US 7,662,114 B2
(45) Date of Patent: Feb. 16, 2010

(54) ULTRASOUND PHASED ARRAYS

(75) Inventors: Ralf Seip, Indianapolis, IN (US);
Wo-Hsing Chen, Fishers, IN (US);
Narendra T. Sanghvi, Indianapolis, IN (US)

(73) Assignee: Focus Surgery, Inc., Indianapolis, IN (US)

( * ) Notice: Subject to any disclaimer, the term of this patent is extended or adjusted under 35 U.S.C. 154(b) by 566 days.

(21) Appl. No.: 11/070,371

(22) Filed: Mar. 2, 2005

(65) Prior Publication Data
US 2005/0240127 A1    Oct. 27, 2005

Related U.S. Application Data

(60) Provisional application No. 60/549,406, filed on Mar. 2, 2004.

(51) Int. Cl.
*A61N 7/00* (2006.01)
*A61B 8/00* (2006.01)

(52) U.S. Cl. .......................................... 601/2; 600/439
(58) Field of Classification Search ................ 600/437, 600/439, 167, 163, 443, 407; 601/1–4; 73/632, 73/609, 610
See application file for complete search history.

(56) References Cited

U.S. PATENT DOCUMENTS

| | | | |
|---|---|---|---|
| 4,005,382 A | 1/1977 | Beaver | |
| 4,074,564 A | 2/1978 | Anderson | |
| 4,084,582 A | 4/1978 | Nigam | |
| 4,161,121 A | 7/1979 | Zitelli et al. | |
| 4,183,249 A | 1/1980 | Anderson | |
| 4,207,901 A | 6/1980 | Nigam | |
| 4,209,706 A | 6/1980 | Nunan | |
| 4,223,560 A | 9/1980 | Glenn | |
| 4,227,417 A | 10/1980 | Glenn | |
| 4,231,373 A | 11/1980 | Waxman et al. | |
| 4,241,412 A | 12/1980 | Swain | |
| 4,241,610 A | 12/1980 | Anderson | |
| 4,248,090 A | 2/1981 | Glenn | |
| 4,257,271 A | 3/1981 | Glenn | |
| 4,274,422 A | 6/1981 | Anderson et al. | |

(Continued)

FOREIGN PATENT DOCUMENTS

CA    1332441    10/1994

(Continued)

OTHER PUBLICATIONS

R. Seip, et al., "Sonablate® 500: A Novel Platform for Transrectal Image-Guided HIFU Treatment of Localized Prostate Cancer," presented at the 32nd Annual Symposium of the *Ultrasonic Industry Association* (UIA), Oct. 2002, 28 pgs.

(Continued)

*Primary Examiner*—Eric F Winakur
*Assistant Examiner*—Lawrence N Laryea
(74) *Attorney, Agent, or Firm*—Reed Smith LLP; William J. McNichol

(57) ABSTRACT

Ultrasound transducers are disclosed which focus acoustic energy at various focal locations while minimizing focal spot degradation and the generation of unwanted on-axis or off-axis energy concentrations through using a generally constant f-number at the various focal locations.

13 Claims, 12 Drawing Sheets

U.S. PATENT DOCUMENTS

| | | |
|---|---|---|
| 4,290,310 A | 9/1981 | Anderson |
| 4,317,370 A | 3/1982 | Glenn |
| 4,324,258 A | 4/1982 | Huebscher et al. |
| 4,325,381 A | 4/1982 | Glenn |
| 4,327,738 A | 5/1982 | Green et al. |
| 4,341,120 A | 7/1982 | Anderson |
| 4,378,596 A | 3/1983 | Clark |
| 4,407,293 A | 10/1983 | Suarez, Jr. et al. |
| 4,410,826 A | 10/1983 | Waxman et al. |
| 4,413,630 A | 11/1983 | Anderson et al. |
| 4,449,199 A | 5/1984 | Daigle |
| 4,586,512 A | 5/1986 | Do-huu et al. |
| 4,620,546 A | 11/1986 | Aida et al. |
| 4,638,436 A | 1/1987 | Badger et al. |
| 4,658,828 A | 4/1987 | Dory |
| 4,664,121 A | 5/1987 | Sanghvi et al. |
| 4,807,633 A | 2/1989 | Fry |
| 4,858,613 A | 8/1989 | Fry et al. |
| 4,917,096 A | 4/1990 | Englehard et al. |
| 4,945,898 A | 8/1990 | Pell et al. |
| 4,951,653 A | 8/1990 | Fry et al. |
| 4,955,365 A | 9/1990 | Fry et al. |
| 5,033,456 A | 7/1991 | Pell et al. |
| 5,036,855 A | 8/1991 | Fry et al. |
| 5,054,470 A | 10/1991 | Fry et al. |
| 5,065,761 A | 11/1991 | Pell |
| 5,080,102 A | 1/1992 | Dory et al. |
| 5,117,832 A | 6/1992 | Sanghvi et al. |
| 5,134,988 A | 8/1992 | Pell et al. |
| 5,149,319 A | 9/1992 | Unger |
| 5,215,680 A | 6/1993 | D'Arrigo |
| 5,219,401 A | 6/1993 | Cathignol et al. |
| 5,247,935 A | 9/1993 | Cline et al. |
| 5,295,484 A | 3/1994 | Marcus et al. |
| 5,316,000 A | 5/1994 | Chapelon et al. |
| 5,391,197 A | 2/1995 | Burdette et al. |
| 5,409,002 A | 4/1995 | Pell |
| 5,409,006 A | 4/1995 | Buchholtz et al. |
| 5,443,069 A | 8/1995 | Schaetzle |
| 5,470,350 A | 11/1995 | Buchholtz et al. |
| 5,492,126 A | 2/1996 | Hennige et al. |
| 5,520,188 A | 5/1996 | Hennige et al. |
| 5,573,497 A | 11/1996 | Chapelon |
| 5,601,526 A | 2/1997 | Chapelon et al. |
| 5,620,479 A | 4/1997 | Diederich |
| 5,630,837 A | 5/1997 | Crowley |
| 5,643,179 A | 7/1997 | Fujimoto et al. |
| 5,676,692 A | 10/1997 | Sanghvi et al. |
| 5,725,482 A | 3/1998 | Bishop |
| 5,762,066 A | 6/1998 | Law et al. |
| 5,769,790 A | 6/1998 | Watkins et al. |
| 5,840,031 A | 11/1998 | Crowley |
| 5,873,902 A | 2/1999 | Sanghvi et al. |
| 5,882,302 A | 3/1999 | Driscoll, Jr. et al. |
| 5,897,499 A * | 4/1999 | Machida ................ 600/443 |
| 5,906,580 A | 5/1999 | Kline-Schoder et al. |
| 5,938,608 A * | 8/1999 | Bieger et al. ............ 600/439 |
| 5,993,389 A | 11/1999 | Driscoll, Jr. et al. |
| 6,016,452 A | 1/2000 | Kasevich |
| 6,083,159 A | 7/2000 | Driscoll, Jr. et al. |
| 6,093,883 A | 7/2000 | Sanghvi et al. |
| 6,193,659 B1 * | 2/2001 | Ramamurthy et al. ...... 600/443 |
| 6,217,530 B1 | 4/2001 | Martin et al. |
| 6,375,634 B1 | 4/2002 | Carroll |
| 6,425,867 B1 | 7/2002 | Vaezy et al. |
| 6,464,638 B1 * | 10/2002 | Adams et al. ............ 600/443 |
| 6,498,945 B1 * | 12/2002 | Alfheim et al. ........... 600/407 |
| 6,500,133 B2 | 12/2002 | Martin et al. |
| 6,575,956 B1 | 6/2003 | Brisken et al. |
| 6,599,256 B1 * | 7/2003 | Acker et al. ................ 601/2 |
| 6,618,620 B1 | 9/2003 | Freundlich et al. |
| 6,626,855 B1 | 9/2003 | Weng et al. |
| 6,656,136 B1 | 12/2003 | Weng et al. |
| 6,666,835 B2 | 12/2003 | Martin et al. |
| 6,676,601 B1 | 1/2004 | Lacoste et al. |
| 6,685,640 B1 | 2/2004 | Fry et al. |
| 6,716,184 B2 | 4/2004 | Vaezy et al. |
| 6,812,204 B1 | 11/2004 | McHale et al. |
| 6,846,290 B2 | 1/2005 | Lizzi et al. |
| 6,875,176 B2 | 4/2005 | Mourad et al. |
| 6,929,608 B1 * | 8/2005 | Hutchinson et al. ......... 600/439 |
| 2001/0008758 A1 | 7/2001 | McHale et al. |
| 2001/0014780 A1 | 8/2001 | Martin et al. |
| 2001/0031922 A1 * | 10/2001 | Weng et al. .............. 600/439 |
| 2002/0035361 A1 | 3/2002 | Houser et al. |
| 2002/0095087 A1 | 7/2002 | Mourad et al. |
| 2002/0102216 A1 | 8/2002 | Lanza et al. |
| 2002/0193785 A1 | 12/2002 | Naghavi et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0060736 A1 | 3/2003 | Martin et al. |
| 2003/0171700 A1 | 9/2003 | Martin et al. |
| 2003/0191396 A1 | 10/2003 | Sanghvi et al. |
| 2003/0204141 A1 | 10/2003 | Nock et al. |
| 2003/0229331 A1 | 12/2003 | Brisken et al. |
| 2004/0030227 A1 | 2/2004 | Littrup et al. |
| 2004/0030268 A1 | 2/2004 | Weng et al. |
| 2004/0039312 A1 | 2/2004 | Hillstead et al. |
| 2004/0059220 A1 | 3/2004 | Mourad et al. |
| 2004/0071664 A1 | 4/2004 | McHale et al. |
| 2004/0106870 A1 | 6/2004 | Mast |
| 2004/0106880 A1 | 6/2004 | Weng et al. |
| 2004/0133192 A1 | 7/2004 | Houser et al. |
| 2004/0167403 A1 | 8/2004 | Nightingale et al. |
| 2004/0210289 A1 | 10/2004 | Wang et al. |
| 2004/0254419 A1 | 12/2004 | Wang et al. |
| 2004/0264293 A1 | 12/2004 | Laugharn, Jr. et al. |
| 2005/0015009 A1 | 1/2005 | Mourad et al. |
| 2005/0025797 A1 | 2/2005 | Wang et al. |
| 2005/0038340 A1 | 2/2005 | Vaezy et al. |
| 2005/0074407 A1 | 4/2005 | Smith |
| 2005/0165298 A1 * | 7/2005 | Larson et al. ............. 600/410 |

FOREIGN PATENT DOCUMENTS

| | | |
|---|---|---|
| CA | 1338240 | 4/1996 |
| EP | 0596513 | 11/1994 |
| WO | WO 93/16641 | 9/1993 |
| WO | WO 98/58588 | 12/1998 |
| WO | WO 99/49788 | 10/1999 |
| WO | WO 01/28623 A2 | 4/2001 |
| WO | WO 01/28623 A3 | 4/2001 |
| WO | WO 01/82777 A2 | 11/2001 |
| WO | WO 01/82777 A3 | 11/2001 |
| WO | WO 01/82778 A2 | 11/2001 |
| WO | WO 02/24050 A2 | 3/2002 |

OTHER PUBLICATIONS

T. Uchida, et al., "Clinical Outcome of High-Intensity Focused Ultrasound (HIFU) for the Treatment of Localized Prostate Cancer: 5-Years Experience", to appear in the *Proc. of the International Symposium on Therapeutic Ultrasound*, 2004, 1 pg. (Abstract).

J.S. Tan, et al., "Design of Focused Ultrasound Phased Arrays for Prostate Treatment," IEEE Ultrasonics Symposium Proceedings, Puerto Rico, 2000, 5 pgs.

T. Gardner, et al., "HIFU Prostatectomy for Prostate Ceancer: The USA Experience", to appear in the *Proc. of the International Symposium on Therapeutic Ultrasound*, 2004, 1 pg. (Abstract).

J. C. Rewcastle, Ph.D., "High Intensity Focused Ultrasound for Prostate Cancer: Clinical Results and Technical Evolution", Whitepaper, 2004, 14 pgs.

T. Uchida, et al., "Transrectal High-Intensity Focused Ultrasound for Treatment of Patients with Stage T1b-2N0M0 Localized Prostate Cancer: A Preliminary Report", *Japanese Journal of Endourology and ESWL*, vol. 16, pp. 108-114, 2003.

T. Uchida, et al., "Transrectal High-Intensity Focused Ultrasound for Treatment of Patients with Stage T1b-2N0M0 Localized Prostate Cancer: A Preliminary Report", *Urology*, 2002, pp. 394-399.

T. Uchida, et al., "Transrectal High Intensity Focused Ultrasound for the Treatment of Localized Prostate Cancer," *International Symposium on Therapeutic Ultrasound*, Seattle, 2002, 9 pgs.

S. Madersbacher, et al., "Effect of High-Intensity Focused Ultrasound on Human Prostate Cancer in Vivo", *Cancer Research* 55, Aug. 1995, pp. 3346-3351.

N. T. Sanghvi, et al., "Noninvasive Surgery of Prostate Tissue by High Intensity Focused Ultrasound: An Updated Report", *European Journal of Ultrasound*, vol. 9; 1999, pp. 19-29.

T. Uchida, et al., "Clinical Outcome of High-Intensity Focused Ultrasound for Treating Benign Prostatic Hyperplasia: Preliminary Report", *Urology*, 1998, pp. 66-71.

L. D. Sullivan, et al., "Early Experience with High-Intensity Focused Ultrasound for the Treatment of Benign Prostatic Hypertrophy", *British Journal of Urology*, 79; 1997, pp. 172-176.

N. T. Sanghvi, et al., "Noninvasive Surgery of Prostate Tissue by High-Intensity Focused Ultrasound", *IEEE Transactions on Ultrasonics, Ferroelectrics, and Frequency Control*. vol. 43, No. 6, Nov. 1996, pp. 1099-1110.

S. Madersbacher, et al., "High-Intensity Focused Ultrasound in Urology", *Japanese Journal of Endourology and ESWL*, vol. 9, No. 1, 1996, pp. 5-15.

F. Fry, et al., "Ultrasound and Microbubbles: Their Generation, Detection and Potential Utilization in Tissue and Organ Therapy—Experimental", *Ultrasound in Medicine & Biology*, vol. 21, No. 9, 1995, pp. 1227-1237.

S. Madersbacher, et al., "Tissue Ablation in Benign Prostatic Hyperplasia with High Intensity Focused Ultrasound", *J. Urology*, vol. 152, Dec. 1994, pp. 1956-1961.

R. S. Foster, et al., "High-Intensity Focused Ultrasound for the Treatment of Benign Prostatic Hypertrophy", *Seminars in Urology*, vol. XII, No. 3, pp. 200-204, Aug. 1994.

S. Umemura, et al., "Coagulation of Swine Liver and Canine Prostate with a Prototype Split-Focus Transducer", *IEEE Ultrasonics Symposium*, 1999, 14 pgs.

J. Wu, et al., "Experimental Studies of Using a Split Beam Transducer for Prostate Cancer Therapy in Comparison to Single Beam Transducer", *IEEE Ultrasonics Symposium*, 1999, 4 pgs.

T. Uchida, "Localized Prostate Cancer Treatment with HIFU", Translated and updated from *The Journal of Highly Advanced Medical Technology*, vol. 15 Mar. 2000, 1 pg.

R. Seip, et al., "Comparison of Split-Beam Transducer Geometries and Excitation Configurations for Transrectal Prostate HIFU Treatments", *IEEE Ultrasonics Symposium Proceedings*, 2001, 4 pgs.

R. Seip, et al., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003, 6 pgs.

R. Seip, et al., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003 (Poster).

K. Ishida, et al., "Development and animal experiment of variable focusing HIFU system for prostate cancer treatment," *Proc. of the International Symposium on Therapeutic Ultrasound*, 2003, 6 pgs.

K. Ishida, et al., "Development and animal experiment of variable focusing HIFU system for prostate cancer treatment," *Proc. of the International Symposium on Therapeutic Ultrasound*, 2003, 18 pgs.

R. Seip, et al., "Annular and Cylindrical Phased Array Geometries for Transrectal High-Intensity Focused Ultrasound (HIFU) using PZT and Piezocomposite Materials," ISTU 4 Conference, Oct. 2004, Kyoto, Japan, 3 pgs.

R. Seip, et al., "High-Intensity Focused Ultrasound (HIFU) Multiple Lesion Imaging: Comparison of Detection Algorithms for Real-Time Treatment Control," *IEEE Ultrasonics Symposium Proceedings*, Munich, Germany, 2002, pp. 1395-1398.

R. Seip, et al., "Real-time Detection of Multiple Lesions during High Intensity Focused Ultrasound (HIFU) Treatments," *International Symposium on Therapeutic Ultrasound*, 2002, 8 pgs.

N.T. Sanghvi, et al., "Decision Theory Applied to High-Intensity Focused Ultrasound (HIFU) Treatment Evaluation," 2003 AIUM Annual Meeting, Jun. 1-4, 2003, Montreal, Quebec, Canada, 24 pgs.

Chen, et al., "The Detection and Exclusion of Prostate Neuro-Vascular Bundle (NVB) in Automated HIFU Treatment Planning Using a Pulsed-Wave Doppler Ultrasound System," 2004 ISTU Conference, Kyoto, Japan, 3 pgs.

R. Seip, et al., "Transurethral High Intensity Focused Ultrasound: Catheter Based Prototypes and Experimental Results," *IEEE Ultrasonics Symposium Proceedings*, Puerto Rico, 2000, 4 pgs.

J. Tavakkoli, et al., "A Laparoscopic HIFU Probe for Kidney Ablation Prior to Partial Nephrectomy," *IEEE Ultrasonics Symposium Proceedings*, Atlanta, 2001, 4 pgs.

N.T. Sanghvi, et al., "Laparoscopically Delivered HIFU for Partial Renal Ablation," 17th International Congress on Acoustics, Sep. 2-7, 2001, Rome, Italy, 2 pgs.

J. Tavakkoli, et al., "Laparoscopic High Intensity Focused Ultrasound: Application to Kidney Ablation," *International Symposium on Therapeutic Ultrasound*, Seattle, 2002, 9 pgs.

J. Tavakkoli, et al., "A Laparoscopic HIFU Probe with Integrated Phased Array Ultrasound Imaging," *Third International Symposium on Therapeutic Ultrasound*, Jun. 2003, Lyon, France, 6 pgs.

J. Tavakkoli, et al., "A Laparoscopic HIFU Probe with Integrated Phased Array Ultrasound Imaging," *International Symposium on Therapeutic Ultrasound*, 2003 (Poster).

R. Seip, et al., "Automated HIFU Treatment Planning and Execution based on 3D Modeling of the Prostate, Urethra, and Rectal Wall", 2004 IEEE Ultrasonics Symposium Proceedings, 4 pgs.

R. Seip, et al., "Automated HIFU Treatment Planning and Execution based on 3D Modeling of the Prostate, Urethra, and Rectal Wall", 2004 IEEE Ultrasonics Symposium Proceedings (Poster).

J.S. Tan, et al., "Ultrasound Phased Arrays for Prostate Treatment", *J. Acoust. Soc. Am.*, vol. 109, No. 6, Jun. 2001, pp. 3055-3064.

R. Seip, et al., "Feasibility Study for the Treatment of Brachytherapy Failure Prostate Cancer using High-Intensity Focused Ultrasound, "*Third International Symposium on Therapeutic Ultrasound*, Lyon, France, Jun. 2003, 6 pgs.

M. Bailey, et al., "Caviation Detection and Suppression in HIFU," *Proc. of the International Symposium on Therapeutic Ultrasound*, 2003, 1 pg. (Poster).

The American Society for Therapeutic Radiology and Oncology Consensus Panel, "Consensus Statement: Guidelines for PSA Following Radiation Therapy," Int. J. Radiation Oncology Biol. Phys., vol. 37, No. 5, 1997, pp. 1035-1041.

N.T. Sanghvi, et al., "Total Prostate Ablation for the Treatment of Localized Prostate Cancer Using Image Guided HIFU," presented at the 2002 IEEE Ultrasonics Symposium. (Poster).

* cited by examiner

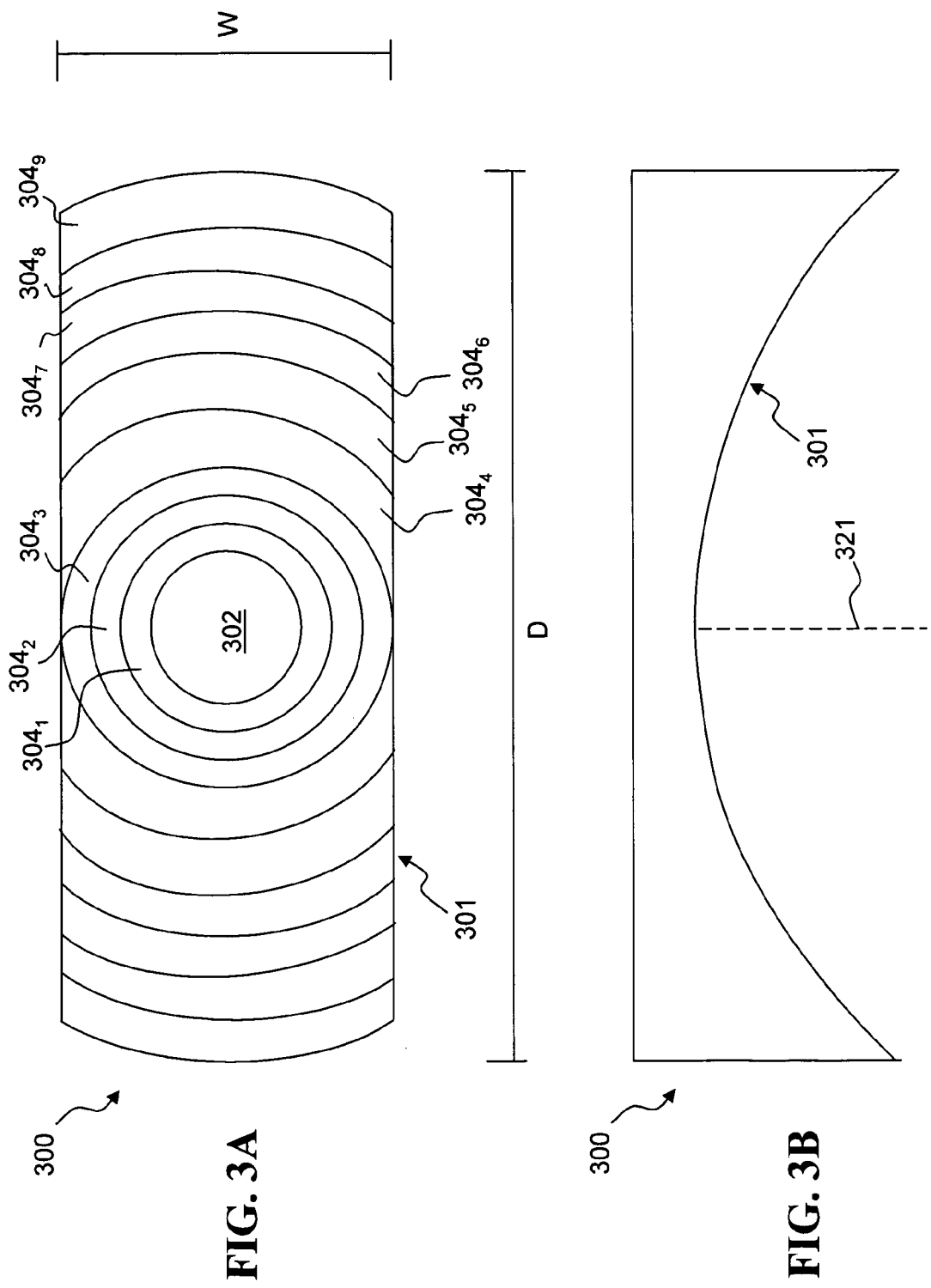

D1

D1

D1

ULTRASOUND PHASED ARRAYS

RELATED APPLICATIONS

This application claims the benefit of U.S. Provisional Patent Application Ser. No. 60/549,406, filed Mar. 2, 2004, titled ULTRASOUND PHASED ARRAY, the disclosure of which is expressly incorporated by reference herein.

NOTICE

This invention was made with government support under grant reference number NIH SBIR IR43 CA81340-01 awarded by National Institutes of Health (NIH) and 2R44 CA081340-02 awarded by NIH. The Government has certain rights in the invention.

BACKGROUND AND SUMMARY OF THE INVENTION

The present invention relates to methods and apparatus for generating, detecting, and/or controlling ultrasound signals and in particular to methods and apparatus for focusing ultrasound signals to provide therapy to tissue at a desired location.

The treatment of tissue with high intensity focused ultrasound ("HIFU") energy is known in the art. As used herein the term "HIFU Therapy" is defined as the provision of high intensity focused ultrasound to a portion of tissue at or proximate to a focus of a transducer. It should be understood that the transducer may have multiple foci and that HIFU Therapy is not limited to a single focus transducer, a single transducer type, or a single ultrasound frequency. As used herein the term "HIFU Treatment" is defined as the collection of one or more HIFU Therapies. A HIFU treatment may be all of the HIFU Therapies administered to a patient, or it may be a subset of the HIFU Therapies administered. As used herein the term "HIFU System" is defined as a system that is at least capable of providing a HIFU Therapy.

The Sonablate® 500 system available from Focus Surgery located at 3940 Pendleton Way, Indianapolis, Ind. 46226 is a HIFU System designed to provide high intensity focused ultrasound therapy to tissue. The Sonablate® 500 system is particularly designed to provide HIFU Therapy to the prostate. However, as stated in U.S. Pat. No. 5,762,066, the disclosure of which are expressly incorporated by reference herein, the Sonablate® 500 system and/or its predecessors may be configured to treat additional types of tissue.

The Sonablate® 500 system generally includes a transducer configured to image the tissue and to subsequently provide a HIFU Treatment to the tissue. The transducer is translated and/or rotated to image various portions of the tissue and to provide HIFU Therapy to various portions of the tissue. The transducer is moved by mechanical methods, such as motors, under the control of a controller. A typical HIFU Treatment includes first imaging the tissue of interest by moving the transducer to image different regions of the tissue. Next, a treatment plan is developed to target various portions of the tissue for treatment. The transducer is then moved to an appropriate location to provide HIFU Therapy to a particular portion of the tissue and the particular portion of the tissue is treated with HIFU Therapy. The treated site is then imaged to determine the effects of the HIFU Therapy. The positioning of the transducer, provision of HIFU Therapy, and post-imaging steps are repeated for each particular portion of tissue which is to be treated.

A need exists for a HIFU System that can treat various portions of tissue at differing focal depths and/or longitudinal locations without the need to move the associated transducer and without the formation of unwanted concentrations of HIFU energy outside of the focal zone, including off-axis. Further, a need exists for a HIFU capable system that can image multiple portions of tissue without the need to move the associated transducer.

In an illustrated embodiment of the present invention, a method of treating tissue with a HIFU System including a transducer is provided. The method comprising the steps of: providing HIFU Therapy to a first portion of the tissue, the first portion being located at a first distance from the transducer; providing HIFU Therapy to a second portion of the tissue, the second portion being located at a second distance from the transducer; maintaining a generally constant f-number with the transducer when providing HIFU Therapy to both the first portion of the tissue and the second portion of the tissue.

In another illustrated embodiment of the present invention a method of conducting a HIFU treatment to a target tissue is provided. The method comprising the steps of: positioning a transducer proximate to target tissue, the transducer having a variable aperture; imaging the target tissue; selecting a plurality of treatment sites within the target tissue to be treated with HIFU Therapy, a first treatment site being located a first distance from the transducer and a second treatment site being located a second distance from the transducer; and providing HIFU Therapy to the plurality of treatment sites with the transducer, the transducer having a first aperture when providing therapy to the first treatment site and having a second aperture when providing therapy to the second treatment site, at least one of an active extent of the first aperture and an active extent of the second aperture being chosen so that a ratio of the second distance to the active extent of the second aperture is generally equal to a ratio of the first distance to the active extent of the first aperture.

In yet another illustrated embodiment of the present invention, a transducer for use with a HIFU System comprising: an active surface having a plurality of transducer elements; and a controller operably coupled to the transducer, the controller being configured to select which transducer elements emit acoustic energy and to control such emissions to focus the acoustic energy at various focal depths so that the active surface has a generally constant f-number at the various focal depths.

In a further illustrated embodiment of the present invention, a method for controlling the emission of acoustic energy from a plurality of transducer elements of a multi-element transducer such that the acoustic energy is focused at a desired location. The method comprising the steps of: determining a phase and an amplitude required for each transducer element; providing a reference continuous wave signal to each transducer element; digitally generating from the reference signal a delayed and pulse-width modulated signal for each transducer element; generating an amplitude modulated analog signal for each transducer element based on the delayed and pulse-width modulated signal for the respective transducer element; and driving the transducer element with the amplitude modulated analog signal.

In still a further illustrated embodiment of the present invention, a method of imaging a targeted tissue and treating portions of the tissue with HIFU Therapy is provided. The method comprising the steps of: providing a transducer having a longitudinal extent at least equal to a longitudinal extent of the targeted tissue, the transducer including a plurality of individually controlled transducer elements; electronically scanning a first sub-aperture of the transducer to generate at least one image of the targeted tissue while the transducer is held in place longitudinally; identifying portions of the targeted tissue for treatment with HIFU Therapy; treating each of the identified portions of the targeted tissue with HIFU Therapy.

Additional features of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 3A is a front view of a spherical transducer including a plurality of annular transducer elements;

FIG. 3B is a side view of the transducer of FIG. 3A;

DETAILED DESCRIPTION OF THE DRAWINGS

Figure 1:
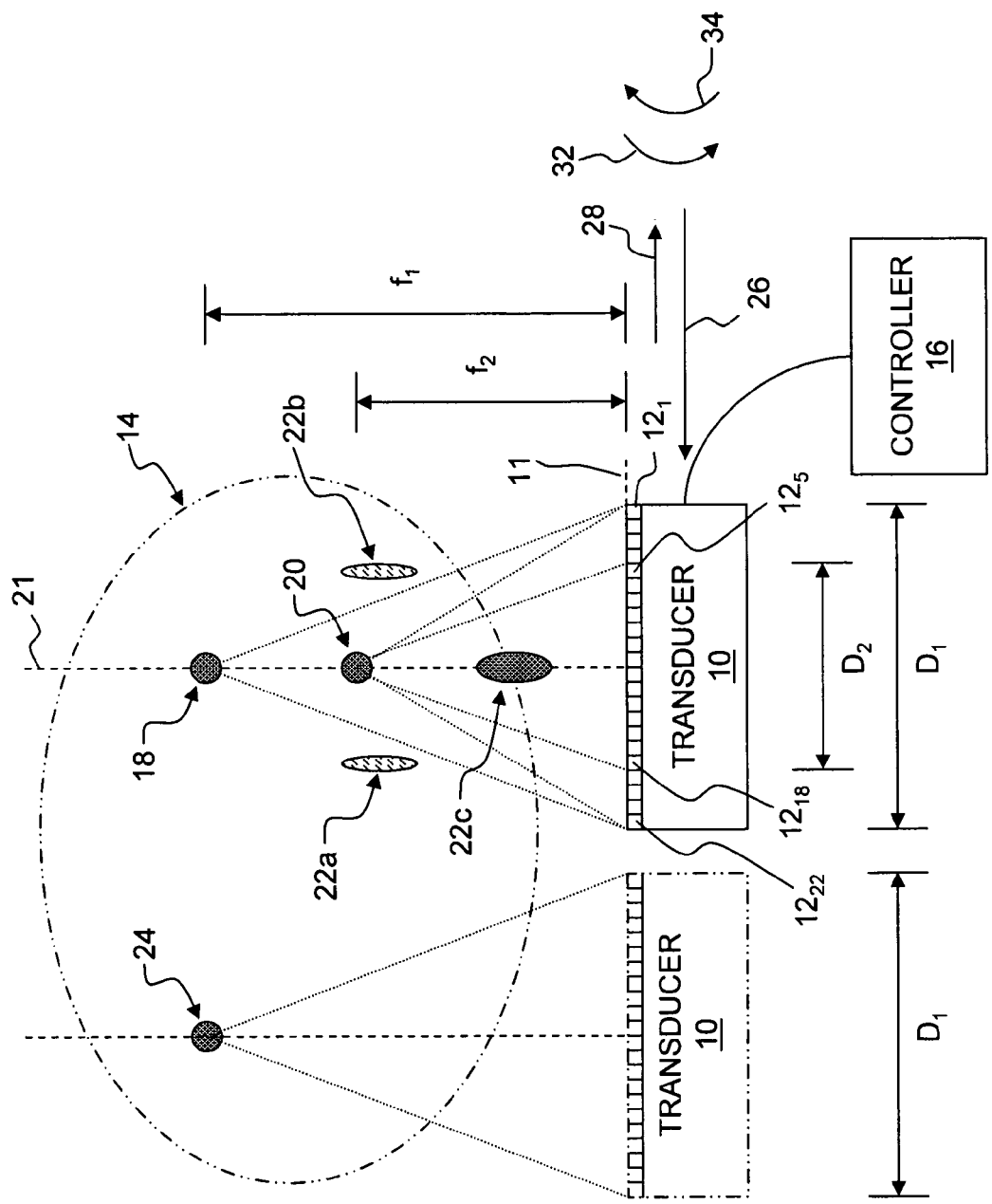
FIG. 1 is a representative view of a first transducer for use in providing HIFU Therapy to and/or imaging of tissue.

Referring to FIG. 1, a transducer 10 is shown. Transducer 10 includes a plurality of transducer elements 12. Transducer 10 is shown to have 22 transducer elements in a row. It should be appreciated that transducer 10 may have more or less transducer elements 12 in the row and/or transducer elements in multiple rows, such as in the case of transducer 400 discussed herein (see FIGS. 4A and 4B). Further, transducer elements 12 are not required to be linearly arranged. For instance, transducer elements 12 may be arranged as concentric rings, such as transducer 300 discussed herein (see FIGS. 3A and 3B). Further, although transducer 10 is shown as being generally flat, transducer 10 may be curved along its longitudinal axis or along its transverse axis or both.

As is known HIFU Therapy requires the emission of a continuous wave ("CW") for a sustained period of time sufficient to ablate the target tissue at the desired location, the focus of transducer 10. For instance, the Sonablate® 500 system typically is set to provide a CW from its associated transducer for about three seconds resulting in ablation of the target tissue at the focus of the transducer. This time period can be increased or decreased depending on the desired lesion size or the desired thermal dose.

A transducer, such as transducer 10 may focus a CW by its physical attributes, such as a center of curvature of the transducer. Transducer 300 (see FIGS. 3A and 3B) is an example of such a transducer. Further, a transducer, such as transducer 10, may focus a CW electronically by delaying (or "phasing"—changing the relative phase of) the CW emitted by various transducer elements 12 relative to the CW emitted by other transducer elements 12. This electronic delaying or phasing causes the emitted waves to constructively interfere or focus at the desired location. This electronic delaying or phasing change may be generated in at least two ways. First, certain transducer elements 12 may emit their respective CW prior to the emission of a CW from other transducer elements. Since each of the CWs are emitted for a sustained period of time, all the CWs will overlap and constructively interfere at the desired location. Second, all transducer elements 12 may emit a respective CW at the same instance of time with at least some of the respective CWs including a predetermined phase delay (0 to $2\pi$) relative to other respective CWs. Due to the predetermined phase delays all emitted CWs will overlap and constructively interfere at the desired location. U.S. Pat. No. 5,520,188 illustrates this principle, the disclosure of which is expressly incorporated by reference herein.

Returning to FIG. 1, each transducer element 12 is capable of generating acoustic energy as a CW having a profile such as sinusoidal. By electronically delaying the CW emitted by each transducer element 12, the emitted CWs may be caused to constructively interfere at a first distance from a plane 11 defined by transducer 10 such that the acoustic energy is said to focus at a location corresponding to first distance. By further electronically phasing the CW emitted by each transducer element 12, the acoustic energy may be focused at a second location. The second location may be inline or on axis with the first location, only closer to or further from transducer 10, or the second location may be off-axis relative to the first location and at same or different depth from transducer 10.

The phase and the amplitude of the continuous acoustic waves from the respective transducer elements 12 is controlled by a controller 16. As stated above, U.S. Pat. No. 5,520,188 provides an exemplary apparatus for controlling the phase and the amplitude of continuous acoustic waves, the disclosure of which is expressly incorporated by reference herein. One use of focused acoustic energy of the respective CWs, as discussed herein, is the provision of HIFU Therapy to a portion of tissue 14.

Referring to FIG. 1, in a first illustrative example, the acoustic energy from the emission of CWs from all twenty-two transducer elements $12_1$-$12_{22}$ is focused at a first focus 18 in tissue 14. Focus 18 is characterized as being on-axis because focus 18 is located along a central axis 21 of transducer 10. It should be noted that by adjusting the phase of the CWs for at least some of the transducer element 12, focus 18 may be intentionally moved off-axis. However, in the illustrated example it is the intention to focus the acoustic energy on-axis at focus 18.

One method of characterizing transducer 10 is the f-number or focusing speed of transducer 10. The f-number (f/#) of transducer 10 is defined as:

$$f/\# = \frac{z}{D}$$

wherein z is the focal length of the transducer (distance from the transducer face that the transducer is attempting to approximate through electronically phasing the transducer elements to the focus, such as focus 18) and D is the extent of the active aperture of the transducer. In the case of the first illustrative example the f-number of transducer 10 is $f_1/D_1$.

In a second illustrative example, acoustic energy from all twenty-two transducer elements $12_1$-$12_{22}$ is focused at a second focus 20 closer to transducer 10 than focus 18 by varying the phase associated with CW of the various transducer elements $12_1$-$12_{22}$. In the case of the second illustrative example, the f-number of transducer 10 is $f_2/D_1$. Since $f_2/D_1$ is smaller than $f_1/D_1$, transducer 10 is characterized as having a faster speed in the second example than in the first example.

It has been found that in some instances utilizing transducer 10 with a higher speed (smaller f-number) that off-axis constructive interference of the various CWs or concentrations of acoustic energy are formed, such as sidelobes 22a and 22b and/or grating lobes 22c along with the intended concentration of energy focused at focus 20. Further, the sharpness or definition of focus 20 is somewhat degraded. This has several drawbacks.

First, the effectiveness of the HIFU Therapy is reduced because some of the energy is lost due to the concentrations of energy off-axis. Second, portions of tissue 14 not intended to be treated during the HIFU Therapy, such as the tissue corresponding to sidelobes 22a and 22b and/or grating lobes 22c, are potentially being subjected to sufficient energy densities to damage the tissue. Third, a poorly defined focus results in the inability to properly locate the focus of the acoustic energy which in surgery applications could result in inadvertent damage to the tissue surrounding the targeted tissue (located at the focus). Fourth, a higher power of acoustic energy is needed to produce a therapeutic amount of acoustic energy to compensate for a lower intensity of acoustic energy at the focus due to the focus being poorly defined and energy being diverted to other unintended focal zones, such as sidelobes 22a and 22b and/or grating lobes 22c.

It has been determined that the formation of unintended off-axis concentrations of energy, such as sidelobes 22a and 22b and grating lobes 22c may be minimized by maintaining a generally constant f-number with transducer 10. For instance, in a third illustrative example only transducer elements $12_5$-$12_{18}$ are used to treat the portion of tissue 14 corresponding generally to focus 20. The delay or phase of the CWs emitted by transducer elements $12_5$-$12_{18}$ are chosen to focus the acoustic energy at focus 20. The f-number of transducer 10 for this third example is $f_2/D_2$ which is generally equal to the f-number in the first illustrative example of $f_1/D_1$. In one embodiment, the amplitude of the acoustic waves emitted by transducer elements $12_5$-$12_{18}$ is increased such that transducer elements $12_5$-$12_{18}$ generate a similar total acoustic power as transducer elements $12_1$-$12_{22}$ at focus 18 in the first illustrative example.

Transducers with an f-number between about 0.8 to about 1.3 are well suited for HIFU Therapy. A preferred f-number is about 1.0. The need to maintain a generally constant f-number in the range of about 0.8 to about 1.3, such as about 1.0, increases as the respective transducer array relies on phasing to focus the array instead of the natural geometry of the transducer array. As such, a generally constant f-number is more important for a flat transducer array, than a cylindrical transducer array and a spherical transducer array. Ideally, the sharpness of a focus would be a constant throughout the tissue 14. However, the shifting of the focus away from a natural focus of the transducer (if it has one) results in a degradation of the focal sharpness and/or the generation of unwanted concentrations of energy are generated outside of the desired focus.

The transducer arrays need to be driven strongly enough to generate total acoustic powers and acoustic intensities at the focus which are capable of ablating tissue. In one embodiment, the CWs emitted by transducer 10 are sinusoidal and have a frequency in the range of 3 MHz to 5 MHz, a duration in the range of 1 second to 10 seconds, with a total acoustic power at the focus in the range of about 5 Watts to about 100 Watts. In a preferred example, the CWs emitted by transducer 10 are sinusoidal with a frequency of about 4.0 MHz and a duration of about 3 seconds. A spherical transducer generally produces the sharpest focus thereby yielding the highest acoustic intensity for a given driving power. However, even with a spherical transducer, maintaining a constant f-number for different focal lengths, such as about 1.0, minimizes focal degradation and/or the generation of unwanted concentrations. In a preferred example, the CWs emitted by a spherical transducer are sinusoidal with a frequency of about 4.0 MHz and a duration of about 3 seconds with a total acoustic power of about 37 Watts at the focus.

In contrast to a spherical transducer, a cylindrical transducer, such as transducer 400, although electronically delayed to approximate a spherical transducer will not generate as sharp of a focus as an actual spherical transducer. The sharpness of the focus from the cylindrical transducer approximating a spherical transducer is about ⅓ the sharpness of a true spherical transducer. As such, about three times the power needs to be provided to drive the cylindrical transducer to achieve similar acoustic intensity at the focus as would be achieved with a spherical transducer. In an example, the cylindrical transducer discussed herein having 826 elements was used to approximate a spherical transducer. The CWs emitted by the cylindrical transducer were sinusoidal with a frequency of about 4.0 MHz and a duration of about 3 seconds with a total acoustic power of about 70 Watts at the focus. The increase in power was required to provide a similar effect on the tissue as the spherical transducer with about 37 Watts. The sharpness of the focus of a flat transducer, such as transducer 10, approximating a spherical transducer is even worse. Therefore even more power needs to be introduced into the tissue to achieve a similar acoustic intensity at the focus with a flat transducer.

In the first and third illustrative examples, transducer elements $12_1$-$12_{22}$ and transducer elements $12_5$-$12_{18}$ each define a respective sub-aperture of transducer 10. The sub-aperture of transducer 10 as explained herein may consist of a subset of transducer elements $12_1$-$12_{22}$, such as transducer elements $12_5$-$12_{18}$, or all of transducer elements $12_1$-$12_{22}$. In general, a sub-aperture of transducer 10 is the active transducer elements utilized for a particular application.

In a fourth illustrative example, a portion of tissue 14 corresponding to focus 24 is to be treated with HIFU Therapy. In order to treat the portion of tissue 14 corresponding to focus 24 transducer 10 is moved in direction 26 by a positioning member 506 (see FIG. 6). Positioning member 506 is configured to mechanically move transducer 10 in directions 26 and 28 and/or to rotate transducer 10 in directions 32, 34. Exemplary positioning members include mechanical linear (adjust in directions 26 and 28) and sector (adjust in directions 32 and 34) motors. Positioning member 506 is instructed by controller 16 as to the location to move transducer 10.

In the case wherein tissue 14 is the prostate and transducer 10 is incorporated into a probe which is transrectally inserted into the patient, transducer 10 is able to treat the prostate at different depths (focuses) without the requirement of the insertion of probes containing different focal length transducers or the movement of transducer 10. However, in such as application transducer 10 probably will require positioning in directions 26 and 28 to treat portions of the prostate not generally in front of transducer 10.

Figure 2:
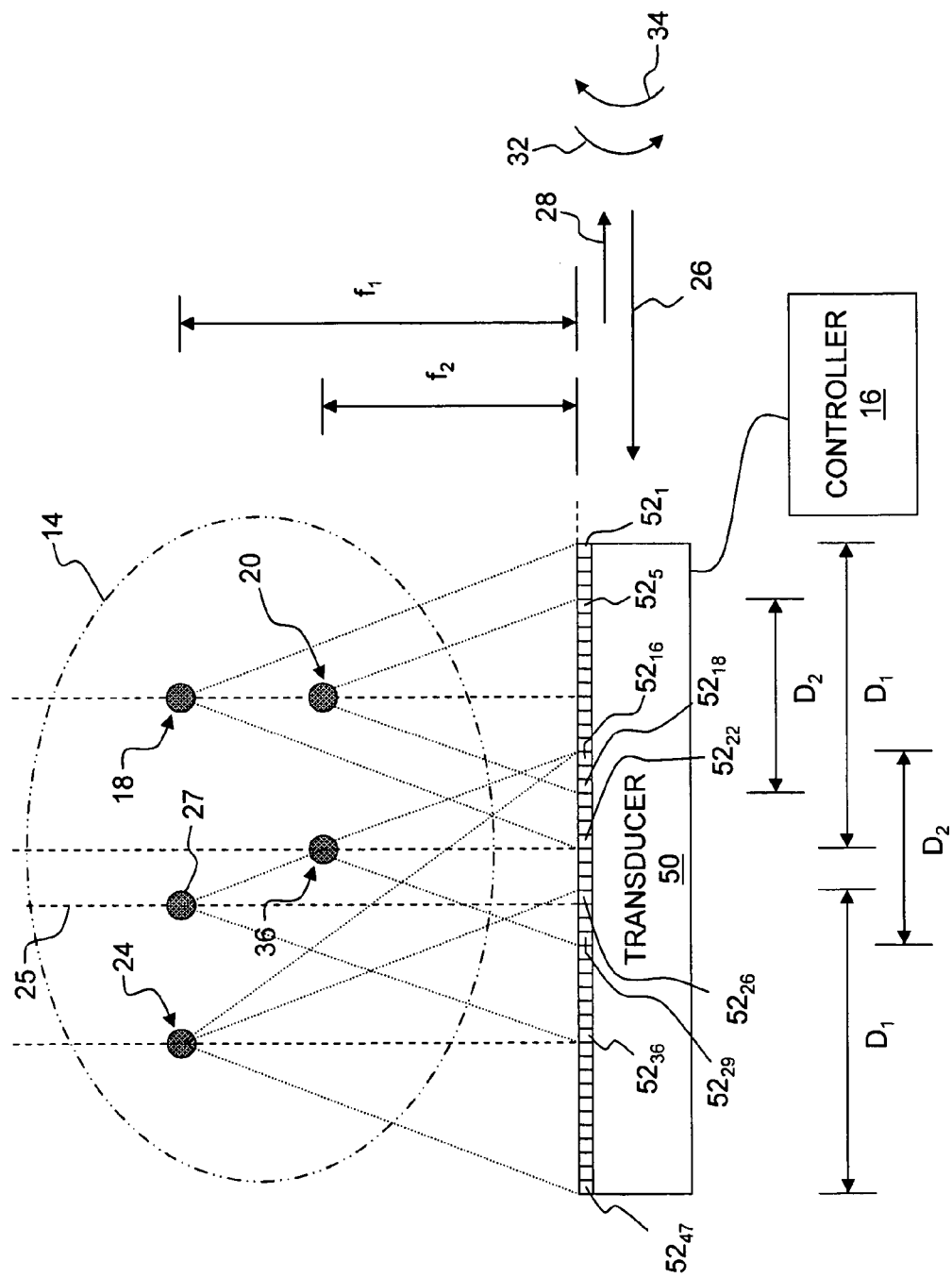
FIG. 2 is a representative view of a second transducer for use in providing HIFU Therapy to and/or imaging of tissue.

Referring to FIG. 2, a second transducer 50 is shown which reduces or eliminates the requirement of a linear positioning member for the movement of transducer 50 in directions 26 and 28. Transducer 50 is generally similar to transducer 10 and includes forty-seven transducer elements. As seen in FIG. 2, controller 16 activates twenty-two transducer elements $52_1$-$52_{22}$ and controls the delay or phase of the CWs emitted by each of transducer elements $52_1$-$52_{22}$ to focus acoustic energy at focus 18. The effective f-number of transducer 50 in this case is $f_1/D_1$. Controller 16 activates fourteen transducer elements $52_5$-$52_{18}$ and controls the delay or phase of CWs emitted by each of transducer elements $52_5$-$52_{18}$ to focus acoustic energy at focus 20. The effective f-number of transducer 50 in this case is $f_2/D_2$.

As seen in FIG. 2, without repositioning transducer 50 in direction 26, acoustic energy is focused at focus 24. Controller 16 activates twenty-two transducer elements $52_{26}$-$52_{47}$ and controls the delay of the CWs emitted by each of transducer elements $52_{26}$-$52_{47}$ to focus acoustic energy at focus 24. The effective f-number of transducer 50 in this case is $f_1/D_1$. The transducer elements $52_1$-$52_{22}$ used to focus energy at focus 18 are completely distinct (but do not have to be distinct as explained herein) from the transducer elements $52_{26}$-$52_{47}$ used to focus energy at focus 24. As such, controller 16 could treat the portions of tissue 14 corresponding to focus 18 and focus 24 in parallel.

Typically, elements $52_{16}$ to $52_{36}$ would be used to create a focus, such as focus 27, along the centerline, axis 25, of this sub-aperture, as shown in FIG. 2. This generates the sharpest focus possible with this geometry. It is also possible to use elements $52_{16}$ to $52_{36}$ to steer the beam off-axis, to create focus 24. When this is done, however, focus quality significantly decreases, focus intensity decreases, and sidelobes and grating lobes appear at other undesired locations in the focal plane (FIG. 1, 22b for example). For this reason, the preferred method to avoid the degradation in focal quality and/or sidelobes and grating lobes is to slide the sub-aperture in such a way that the focus is again located along the centerline of the sub-aperture, for example by using elements $52_{22}$ to $52_{47}$. This way, the quality and shape of the focus 24 is generally the same as that achieved with elements $52_{16}$ to $52_{36}$ (focus 27), or elements $52_1$ to $52_{22}$ (focus 18), for example. Further, the sub-aperture used $52_{16}$ to $52_{36}$ should have generally the same f-number as the sub-aperture used for focus 18 which is at the same depth (transducer elements $52_1$ to $52_{22}$).

As such, a preferred method for treating various portions of tissue 14 with HIFU Therapy is for each treatment site (a treatment site corresponds to a portion of the tissue to be treated) a sub-aperture that is generally centered on that treatment site is selected. The activated sub-aperture is then used to provide HIFU Therapy to the treatment site. If the next treatment site is along the same axis, the size of the sub-aperture is adjusted to treat the next treatment site with HIFU Therapy such that the f-number of the sub-aperture is generally constant, such as equal to about 1.0. If the next treatment site is not centered along the same axis, a new sub-aperture is selected such that the treatment site is centered along the axis of the new sub-aperture. Again the size of the new sub-aperture is selected such that the f-number of the new sub-aperture is generally constant with the previous sub-aperture, such as equal to about 1.0.

However, it is not required that the various transducer elements $52_1$-$52_{47}$ be used only in set combinations of transducer elements $52_1$-$52_{47}$. For instance, controller 16 activates fourteen transducer elements $52_{16}$-$52_{29}$ and controls the delay or phase of the CWs emitted by each of transducer elements $52_{16}$-$52_{29}$ to focus acoustic energy at focus 36. The effective f-number of transducer 50 in this case is $f_2/D_2$. As is apparent from this example, transducer elements 52 may be used to treat more than one portion of tissue 14 even portions of tissue 14 which are not in line with each other, such as focus 20 and 36 and which are not in line with each other and not at the same depth such as focus 18 and focus 36. For example, transducer elements $52_{16}$-$52_{18}$ are used both in the focusing of acoustic energy at focus 20 and at focus 36. However, in such situations wherein the various sub apertures of transducer 50 overlap, the portions of tissue 14 may not be treated in parallel.

In a preferred embodiment transducer 10 and transducer 50 each contains more than a single row of transducer elements 12. A first exemplary embodiment 300 of transducer 10 is shown in FIGS. 3A and 3B. Referring to FIG. 3A, transducer 300 has an active surface 301 which includes a central transducer element 302 and nine annular transducer elements $304_{1-9}$ which are each capable of providing HIFU Therapy.

The active surface 301 of transducer 300 conforms generally in shape to a sphere, as shown in FIG. 3B. As such, if each of transducer elements 302 and $304_{1-9}$ or a combination thereof generated CWs in phase, transducer 300 due to its geometric shape would naturally focus the emitted acoustic energy at the center of the sphere to which the face 301 conforms. However, as stated above in connection with transducer 10, by electronically phasing the CWs emitted by the active transducer elements of transducer elements 302 and $304_{1-9}$ acoustic energy may be focused at different focus spots along axis 321. Further, by selecting which transducer elements will be used to emit acoustic energy, the f-number of transducer 300 can be maintained generally constant for various focal lengths of transducer 300.

In one embodiment, transducer element 302 and transducer elements $304_{1-9}$ are used to provide HIFU Therapy to tissue 14. In another embodiment, transducer element 302 is used for imaging tissue, such as tissue 14, and transducer elements $304_{1-9}$ are used to provide HIFU Therapy. In one example, transducer element 302 is specifically designed for imaging applications. In yet another embodiment, transducer element 302 is used for imaging and transducer element 302 and transducer elements $304_{1-9}$ are used to provide HIFU Therapy to tissue 14. U.S. Pat. No. 5,520,188 describes a controller for controlling multi-element annular transducers such as transducer 300, the disclosure of which is expressly incorporated herein by reference.

Although transducer 300 is shown with a central element 302 and nine annular elements $304_{1-9}$, additional or fewer annular elements may be used. In one example, transducer 300 includes a central element 302 and nine annular elements 304 and has a size of about 40 mm (D) by about 22 mm (W) (used for operation at 2.0 MHz). Central element 302 is about 10 mm in diameter. Face 301 has a spherical radius of curvature of about 45 mm. In another example, transducer 300 includes a central element 302 and seventeen annular elements 304 and has a size of about 35 mm (D) by about 22 mm (W) (used for operation at 3.5 MHz). Central element 302 is about 10 mm in diameter. Face 301 has a spherical radius of curvature of about 35 mm. In yet another example, transducer 300 includes a central element 302 and twenty annular elements 304 and has a size of about 50 mm (D) by about 22 mm (W) (used for operation at 4.0 MHz). Central element 302 is about 10 mm in diameter. Face 301 has a spherical radius of curvature of about 45 mm.

As stated above, by electronically phasing the CWs from various transducer elements 302 and/or $304_{1-9}$ transducer 300 may be used to treat tissue at various focal lengths. Further, f-number of transducer 300 may be maintained generally constant for various focal lengths by selecting which transducer elements are used in the treatment of tissue at a given focal length. However, transducer 300 may not be used to treat tissue at other spaced apart longitudinal locations (offset in one of directions 26 and 28 in FIG. 1) while still maintaining the focus of the acoustic energy on-axis 321 of transducer 300. As such, transducer 300 requires a longitudinal positioning member, such as a motor, to move transducer 300 in directions 26 and 28.

Figure 4A:
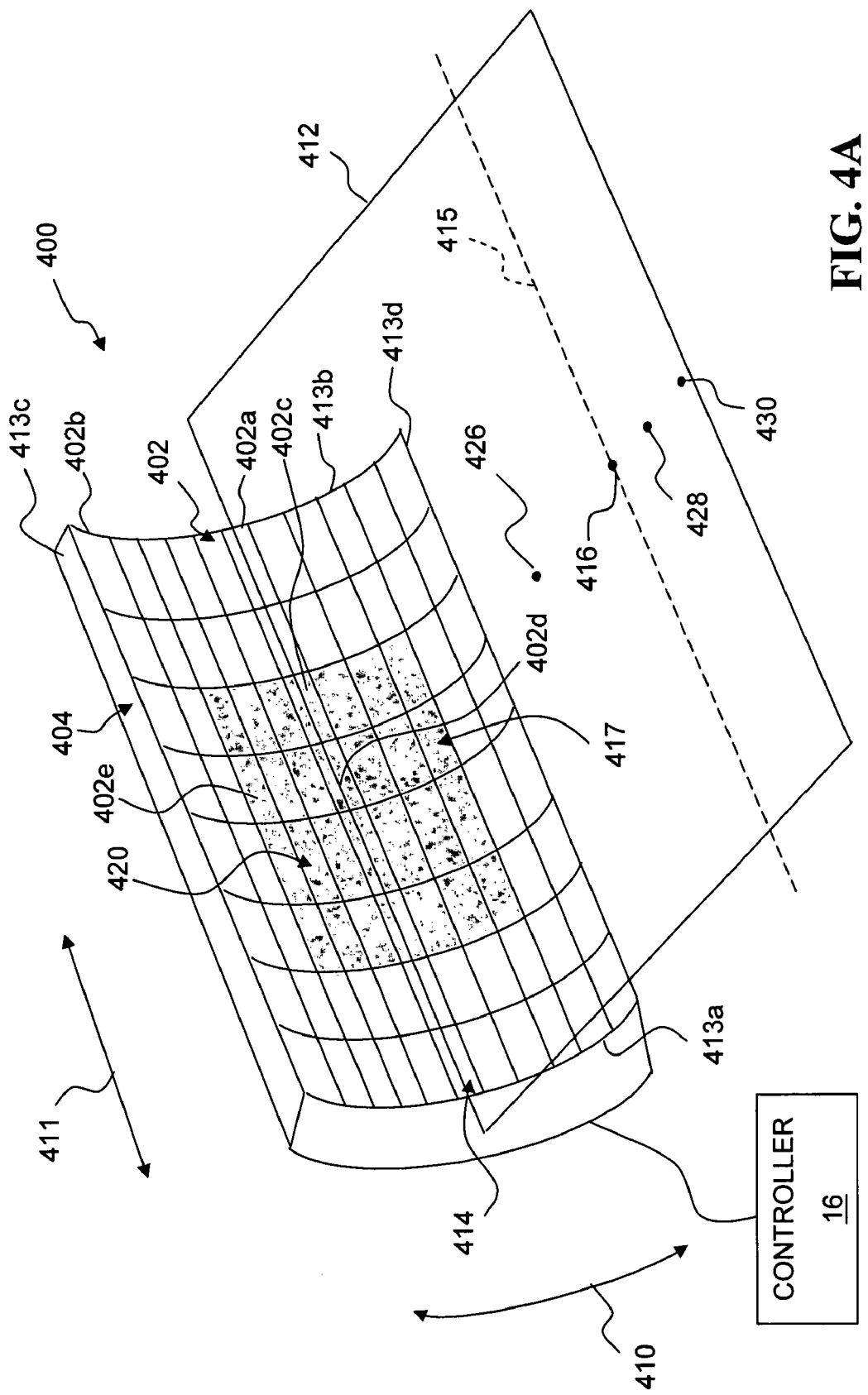
FIG. 4A is an isometric view of a cylindrical transducer including a plurality of linearly arranged transducer elements.
Figure 4B:
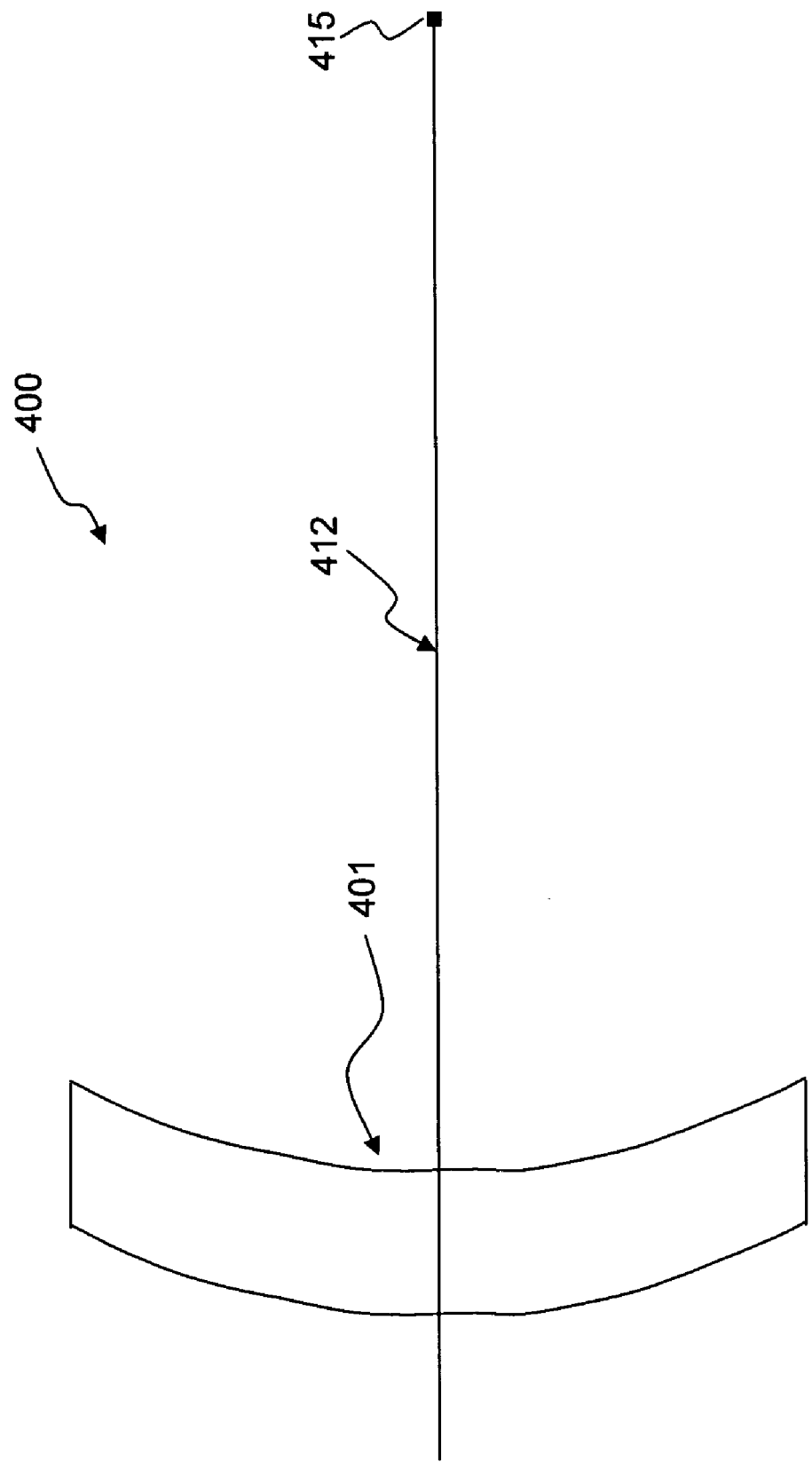
FIG. 4B is a side view of the transducer of FIG. 4A.

Referring to FIGS. 4A and 4B, an exemplary transducer 400 is shown which can be used as either transducer 10 or transducer 50. Transducer 400 includes a face 401 including a plurality of transducer elements 402. Transducer elements 402 are illustratively arranged in eleven rows of eight transducer elements each. However, transducer 400 is not limited to the number of rows of transducer elements or the number of elements in each row. In one embodiment, transducer 400 includes a different number of elements 402 in different rows and/or different sizes or shapes of elements 402. In a preferred example, transducer 400 is about 80 mm in length and about 22 in width. In this example, transducer 400 includes about 826 elements arranged in six rows of 116, 138, 159, 159, 138, and 116 elements each. Further, in this example, face 401 is generally cylindrical along the rows of transducer elements 402, the cylinder having a radius of curvature of about 40 mm. In the preferred example, transducer elements 402 are generally rectangular and have shorter extent along the longitudinal extent of transducer 400 than in the curved direction of transducer 400. This permits a finer resolution for phasing the elements of a given sub-aperture of transducer 400 to approximate a spot instead of the natural focus of the sub-aperture, a line. The finer resolution is derived from the fact that more transducer elements along the longitudinal extent (for a given sub-aperture extent) can have their own phase and amplitude parameters assigned thereto. This assists in maintaining the sharpness of the focus spot and thus provides a better approximation of a spherical transducer.

Figure 5A:
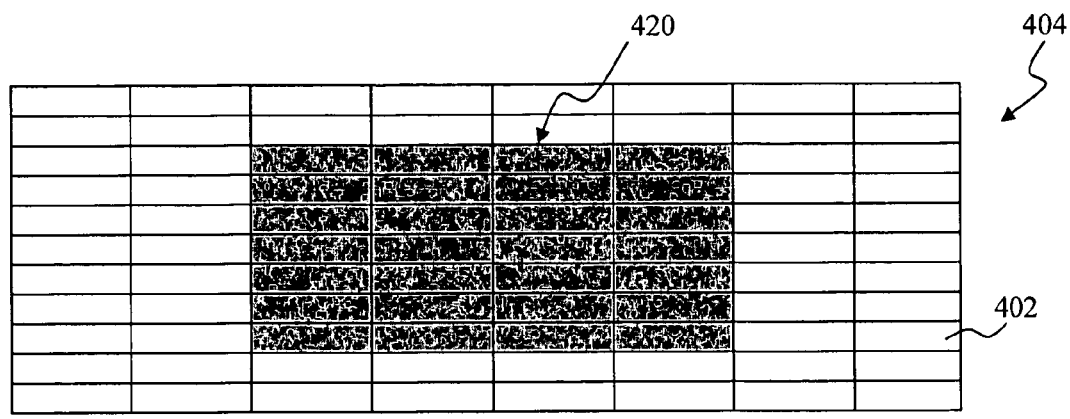
FIGS. 5A-5C represent representative sub-apertures of the transducer of FIG. 4 used for providing HIFU Therapy.

The f/number of transducer 400 is defined as:

$$f/\# = \frac{z}{D}$$

wherein z is the focal length of transducer 400 (distance from transducer face 401 to focus, such as focus 416) and D is the extent of the active aperture of the transducer (see FIG. 5A). In the case of an electronically delayed or phased transducer z is the distance from the transducer face that the transducer is attempting to approximate to the focus.

As stated above, by maintaining a generally constant f-number, transducer 400 is able to maintain a relatively sharp focus spot at various focal lengths. A sharp focus permits the ultrasound energy in the CWs emitted by transducer elements 402 to be reliably focused at a given spot and reduces sidelobes and grating lobes. As stated above, the maintaining of the generally constant f-number results in a sharper focus of the CWs emitted from transducer 400 and minimizes the likelihood of off-axis concentration of acoustic energy so that a higher percentage of the emitted acoustic energy is concentrated at the given focus. As such, the overall amount of ultrasound energy emitted by transducer 400 to provide the required therapeutic amount of energy at the focus is lessened due to the tightness of the focus and the minimization of the unwanted concentrations of energy outside of the desired focus, such as sidelobes 22a and 22b and grating lobes 22c.

Referring to FIG. 4A, transducer 400 includes a plurality of transducer elements 402 arranged in an array 404. Each transducer element 402 is configured to emit ultrasound energy from a face 401 and/or to detect the reception of ultrasound energy at face 401 (for imaging applications). Each transducer element 402 is operably controlled by a controller, such as controller 16. It should be noted that the transducer elements are shown as rectangular elements, however it is contemplated to have other element shapes and configurations, such as rectangular elements of different sizes or ring elements arranged in concentric relation to each other.

The shape of array 404 may be generally flat, generally cylindrical (constant curvature in one direction), generally elliptical (a first constant curvature in a first direction and a second constant curvature in a second direction), or generally spherical (constant curvature in two directions). The shape of array 404 may focus ultrasound energy with the CWs emitted by transducer elements 402. For example, a generally cylindrical array 404 (as shown in FIG. 4A) will naturally focus ultrasound energy from elements 402 along axis 415 of the cylindrical array 404 assuming all elements 402 emit ultrasound or acoustic energy at generally the same instant in time and with generally the same phase. Further, as stated herein by delaying or phasing the emission of CWs of transducer element 402 relative to each other, the CWs may be focused at other locations. For instance, a generally flat array may approximate the focus of a cylindrical array by phasing the CWs from the central transducer elements, such as element 402a in FIG. 4A relative to perimetral transducer elements, such as element 402b in FIG. 4A, near the edge of array 404.

Referring to FIG. 4A, transducer 400 is illustratively shown as a generally cylindrical transducer having a generally constant curvature along a first direction 410 and generally zero curvature along a second direction 411 such that ultrasound energy emitted from any of transducer element 402 intersects a plane 412 passing through a central row 414 of transducer elements 402 generally along axis 415. However, as explained in more detail below by phasing the emission of CWs from some of transducer elements 402 the acoustic energy may be generally focused to a spot 416. Spot 416 is shown as lying on axis 415, however, as known in the art, spot 416 may be located at other points above, on, or below plane 412 by electronically altering the delay of the CW of the respective transducer elements 402.

Referring to FIG. 5A, a first sub-aperture 420 of transducer elements 402 is shown. Sub-aperture 420 may include any number of transducer elements 402 up to all of transducer elements 402. Controller 16 controls the transducer elements 402 which define sub-aperture 420 by controlling which transducer elements 402 emit a CW of ultrasound energy. As such, the location of sub-aperture 420 along direction 410 and along direction 411 may be adjusted by controller 16 (centered on array 404, offset from center toward one or more of edges 413a, 413b, 413c, 413d) as well as the size (number of elements 402) of sub-aperture 420.

Therefore, controller 16 may longitudinally move sub-aperture 420 along direction 410 and/or laterally move sub-aperture 420 along direction 411 without requiring the movement of transducer 400. Further, by simply moving sub-aperture 420 the desired constant f-number and desired focal shape is maintained. As stated above in connection with transducer 50 this permits for the on-axis treatment of longitudinally spaced apart portions of tissue 14. Further, as discussed herein, this permits the ability to image tissue 14 through a plurality of sub-apertures.

Controller 16 controls the transducer elements 402 of sub-aperture 420 to focus the ultrasound energy of the emitted CWs at focus 416 by electronically phasing the CWs from central elements 402d relative to perimetral elements 402c for a given row 414.

Controller 16, as stated above, may further control the focus spot of sub-aperture 420 to be above, below, or at a different location or plane 412 by electronically phasing the CWs from some elements 402 within sub-aperture 420 relative to other elements 402 within sub-aperture 420. For instance, to focus energy at focus 426 controller 16 phases the emission of the CWs from central elements 402d relative to the CWs from perimetral elements 402c for a given row 414 and phases the emission of CWs from central elements 402d relative to the CWs from perimetral elements 402e for a given column 417. By delaying the emission of the CWs as described, array 404 appears to have a greater curvature in direction 410 and the resultant ultrasound energy focuses on plane 412 at focus spot 426 closer to array 404 than focus 416.

In another example energy is focused at focus 428 by electronically phasing the emission of CWs from some elements 402 within sub-aperture 420 relative to the CWs from other elements 402 within sub-aperture 420. For instance, to focus energy at focus 428 controller 16 delays the emission of CWs from central elements 402d relative to the CWs from perimetral elements 402c for a given row 414 (however the delay is lower than the delay is set to be less than the delay for focus 416 and focus 426) and delays the emission of CWs from perimetral elements 402e relative to the CWs of the central elements 402d for a given column 417. By delaying the emission of the CWs as described, array 404 appears to have a smaller curvature in directions 410, 411 and the resultant ultrasound energy focuses on plane 412 at focus spot 428 further from array 404 than focus 416.

As the f-number of transducer 400 is decreased due to the placement of the focus of sub-aperture 420 closer to array 404 while maintaining the same number of transducer elements in respective sub-aperture 420, the focus spot, such as focus spot 426, is reduced in size compared to the focus spot for configurations of transducer 400 having a higher f-number, such as the configuration corresponding to focus spot 416, 428, and 430. Further, sidelobes or regions of focused ultrasound energy begin to appear at locations off-axis from the focus spot or in front of the focus spot when the f-number of transducer 400 is decreased, such as sidelobes 22a, 22b and grating lobe 22c in FIG. 1. A small focus spot results in less tissue treated with the ultrasound energy which in surgery applications could result in poor treatment to the tissue surrounding the target tissue (located at the focus). Additionally, a higher power of ultrasound energy is needed to produce a therapeutic amount of ultrasound energy to compensate for the focus spot being small. Further, the presence of the sidelobes and/or grating lobes results in a loss of ultrasound energy and the potential for damage to tissue in the region of the sidelobes and/or grating lobes.

In general, bringing the focal spot closer to the transducer (without changing the aperture of the transducer—in effect changing the f-number) reduces the performance of the system in at least three ways: (1) a smaller focus; (2) the generation of grating lobes and sidelobes on-axis as well as off-axis; and (3) the acoustic power at the focus is reduced. Moving the focal spot farther from the transducer (without changing the aperture of the transducer—in effect changing the f-number) reduces the performance of the system in at least two ways: (1) a larger focus with less definition and (2) the acoustic intensity at the focus is reduced. Focusing the transducer off-axis (without moving the sub-aperture) reduces the performance of the system in at least three ways: (1) a less-defined focus; (2) the generation of grating lobes and/or sidelobes; and (3) the acoustic intensity at the focus is reduced.

Figure 5B:
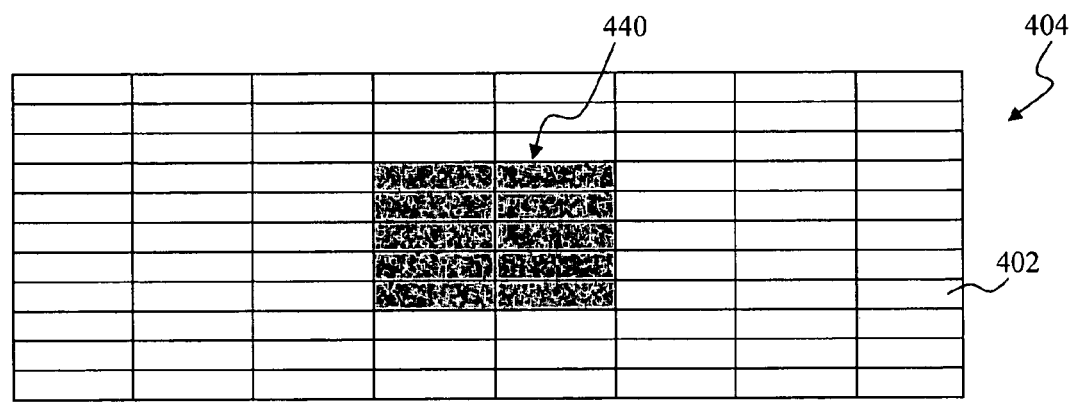
Figure 5C:
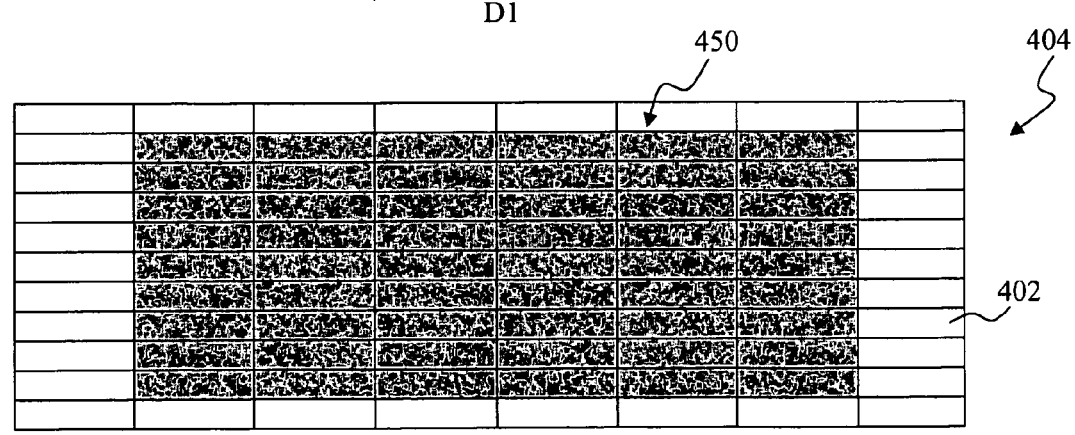

It has been found that the definition or tightness of the focus spot and the minimization of sidelobes may be achieved by varying the extent of the sub-aperture 420 for different focus spots such that the f-number or speed of transducer 400 remains generally constant. For instance, assuming sub-aperture 420 (see FIG. 4A and FIG. 5A) provides a high quality focus spot 416 and minimizes the presence of sidelobes, then similar results can be achieved for focus spots 426 by decreasing the extent of sub-aperture 420 by the same percentage as the decrease in the focal length for focus 426 over the focal length of focus 416, such as by using sub-aperture 440 (see FIG. 5B). Further, similar results can be achieved for focus spot 428 by increasing the extent of sub-aperture 420 by the same percentage as the increase in the focal length for focus 428 over the focal length for focus 416, such as by using sub-aperture 450.

By maintaining a tight focus spot and minimizing the likelihood of sidelobes the potential for unintentional tissue damage is reduced. Further, the maintenance of a tight focus allows for a lower power ultrasound energy to be used because more energy is concentrated at the focus. Another advantage of the tight focus spot is the ability to focus ultrasound energy close to tissue that needs to be preserved, such as the rectal wall, to provide therapy to tissue requiring treatment, such as the prostate tissue which is adjacent the rectal wall, without damaging the rectal wall.

The above described transducer 400 and associated controller 16, in one embodiment are incorporated into an ultrasound therapy apparatus, such as the Sonablate® 500 HIFU available from Focus Surgery located at 3940 Pendleton Way, Indianapolis, Ind. 46226.

Figure 6:
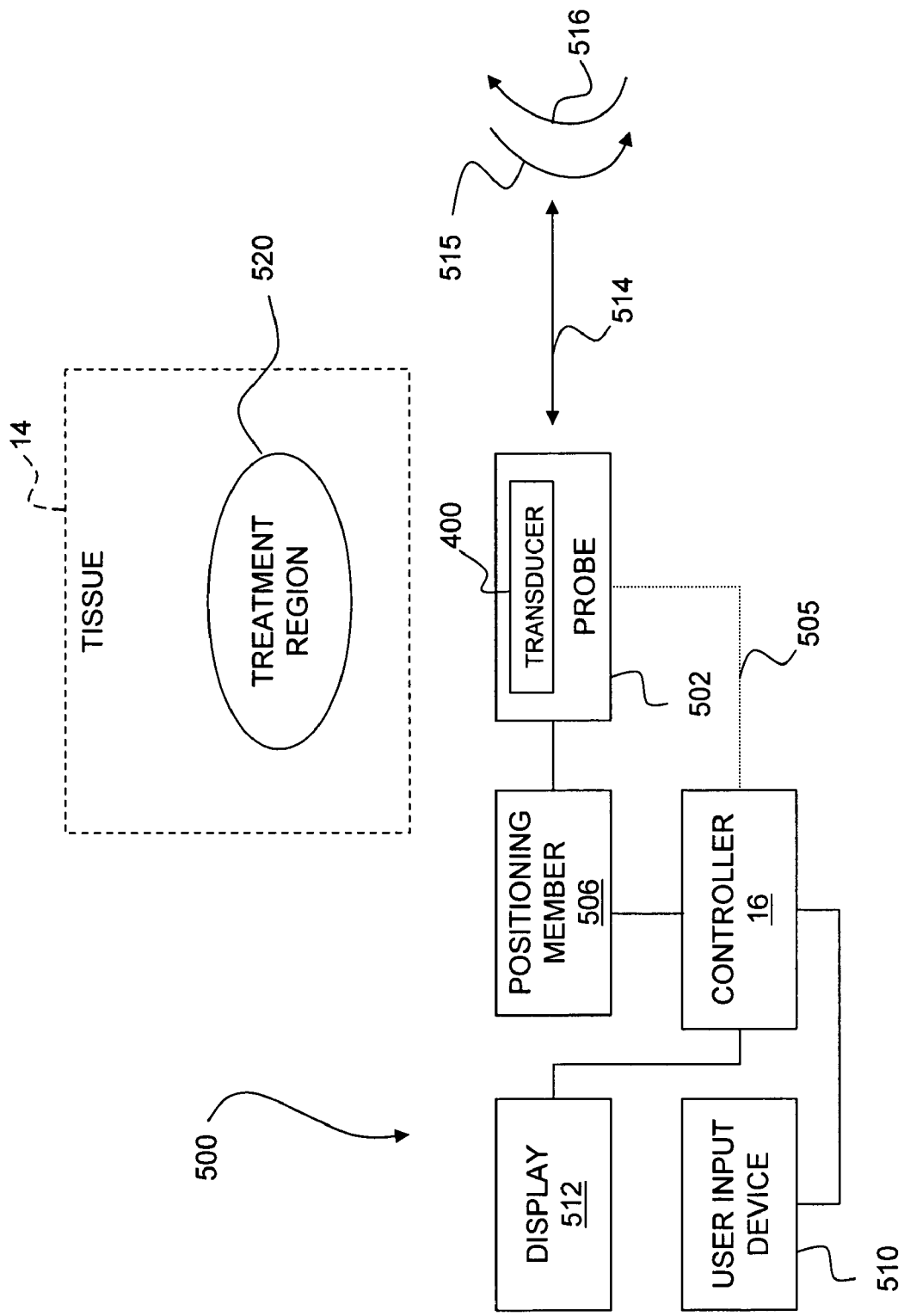
FIG. 6 is a schematic view of an exemplary HIFU System incorporating the transducer of FIG. 4A which is configured to focus HIFU energy at multiple focal lengths while maintaining a generally constant f-number.

Referring to FIG. 6 an exemplary HIFU System 500 incorporating transducer 400 is illustrated. HIFU System 500 includes a probe 502 including transducer member 400, a positioning member 506, controller 16 operably coupled to probe 502 and the positioning member 506, a user input device 510, and a display 512. Probe 502 is operably connected to controller 16 through positioning member 506. However, as indicated by line 505 probe 502 may be directly connected with controller 508. Positioning member 506 is configured to linearly position transducer member 400 along line 514 and to angularly position transducer member 400 in directions 515, 516.

Transducer member 400 is positioned generally proximate to a region of tissue 14. In the case of the prostate, transducer 400 is positioned generally proximate to the prostate by the transrectal insertion of probe 502. Transducer member 400 is moved by positioning member 506 and controlled by controller 16 to provide imaging of at least a portion of tissue 14 including at least one treatment region 520 and to provide HIFU Therapy to portions of the tissue within the at least one treatment region 520. As such, HIFU System 500 may operate in an imaging mode wherein at least a portion of tissue 14 may be imaged and in a therapy mode wherein HIFU Therapy is provided to portions of tissue 14 within at least one treatment region 520.

It should be noted that for HIFU applications wherein the longitudinal extent of transducer 400 is sufficient to cover the entire treatment region 520 of tissue 14 positioning member 506 does not require the ability to position transducer 400 along line 514 during the HIFU Treatment. However, it may be beneficial to retain the ability to position transducer 400 along line 514 to assist in the initial setup of HIFU System 500.

Figure 5D:
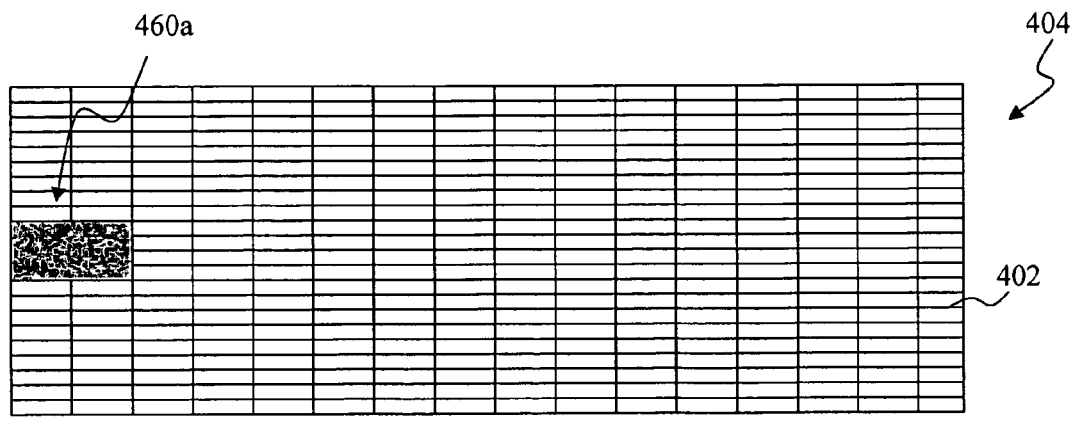
FIGS. 5D-5F represent representative sub-apertures of the transducer of FIG. 4 used to image the tissue of interest.
Figure 5E:
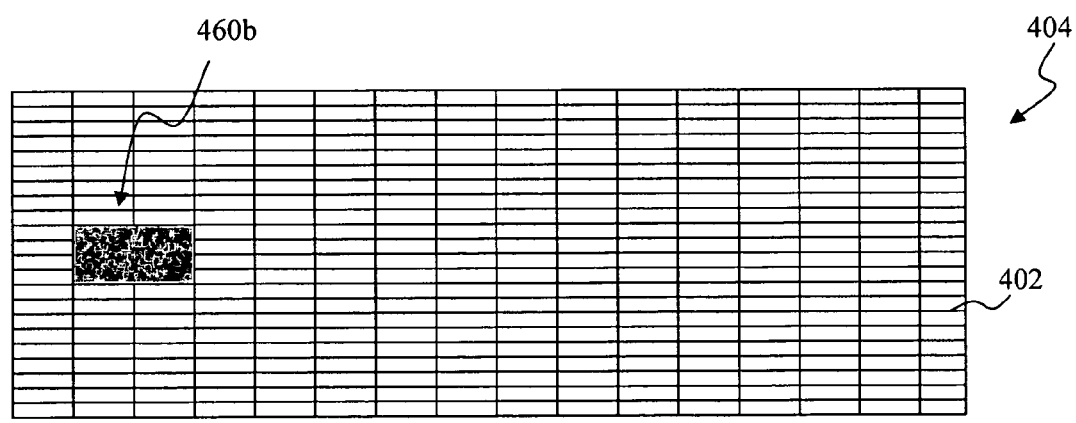
Figure 5F:
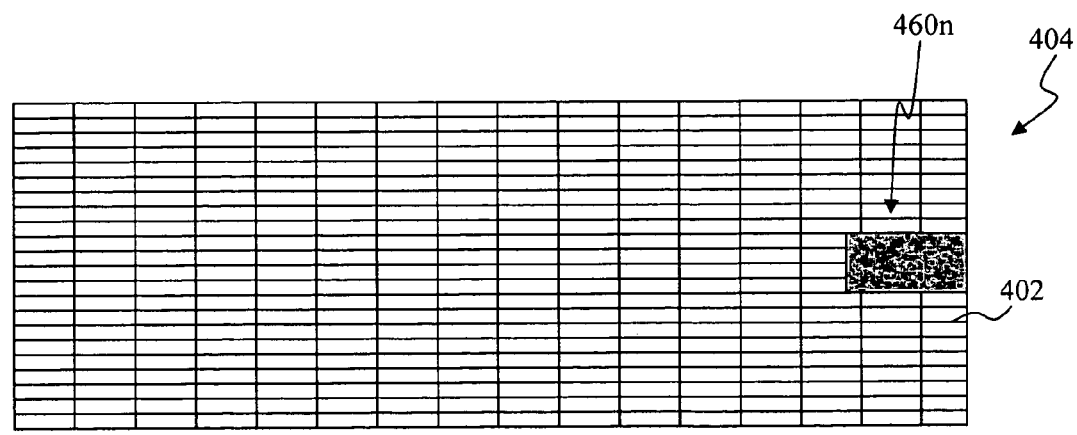
Figure 5G:
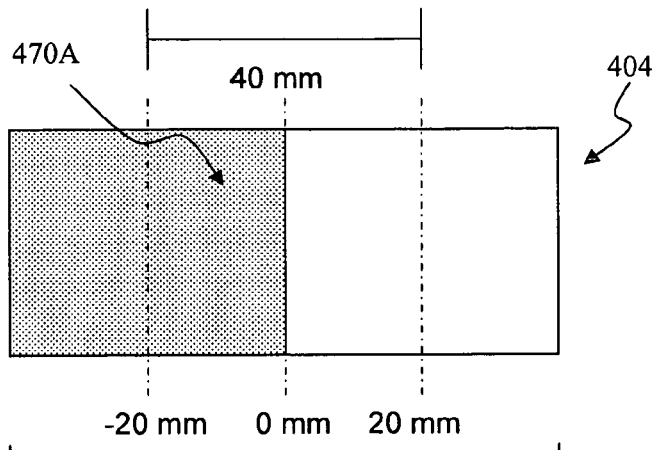
FIGS. 5G-5I represent representative sub-apertures of one example of the transducer of FIG. 4 moving a sub-aperture to center respective portions of the tissue to treat.
Figure 5H:
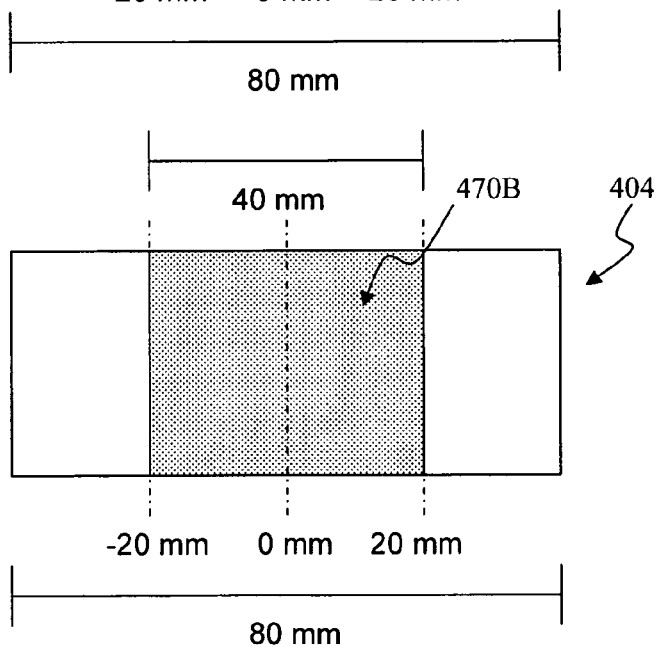
Figure 5I:
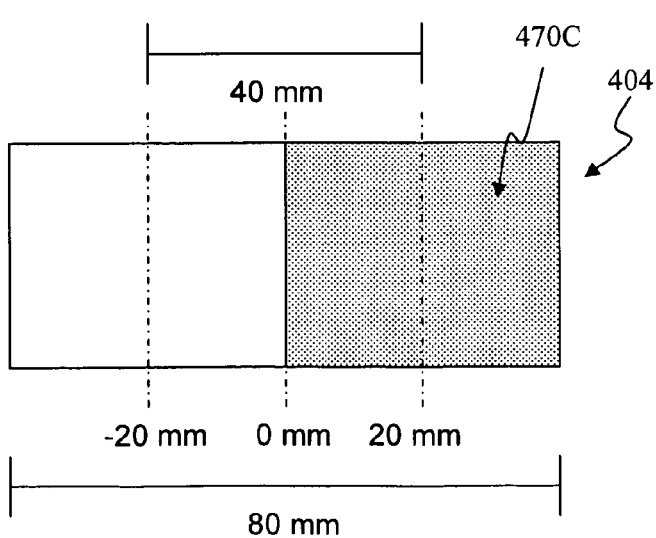

In a preferred example wherein the target tissue is the prostate and assuming that transducer 400 is about 80 mm in length, positioning member 506 does not need to move transducer 400 during the HIFU treatment. In one example for the treatment of the prostate, transducer 400 has the ability to focus in the range of about 25 mm to about 45 mm, in depth, and the ability to longitudinally move a respective sub-aperture about 20 mm in either longitudinal direction. FIGS. 5G, 5H, and 5I illustrate the movement of a sub-aperture 470 from −20 mm to +20 mm for the preferred example wherein transducer 400 is about 80 mm in length and includes 826 transducer elements (transducer elements not shown). Sub-aperture 470 is approximately 40 mm in length in all three cases (constant f-number). So assuming sub-aperture 470 is focusing at a location about 40 mm from the face of transducer 400, the f-number of transducer 400 in each of FIGS. 5G (sub-aperture 470A), 5H (sub-aperture 470B), and 5I (sub-aperture 470C) is about 1.0.

In one embodiment, controller 16 is configured to image tissue 14 with transducer 400 prior to the application of HIFU Therapy to various portions of tissue 14. Referring to FIGS. 5D-5F, one example method of imaging tissue 14 is shown (It should be noted that the number of transducer elements 402 have been double for the examples shown in FIGS. 5D-5F). Referring to FIG. 5D, at a first instance a sub-aperture 460a of transducer 400 is activated. A short pulse of ultrasound energy is emitted from the transducer elements 402 which comprise sub-aperture 460a. The same transducer elements of sub-aperture 460a are then used to detect reflected energy from portions of tissue 14. This reflected energy is then presented as a single line of a b-mode image of tissue 14 as is well known in the art.

Next, referring to FIG. 5E, at a second instance a sub-aperture 460b of transducer 400 is activated. A short pulse of ultrasound energy is emitted from the transducer elements 402 which comprise sub-aperture 460b. The same transducer elements of sub-aperture 460a are then used to detect reflected energy from portions of tissue 14. This reflected energy is then presented as a single line of a b-mode image of tissue 14 as is well known in the art. This process of electronically scanning sub-aperture 460 continues until it is completed with sub-aperture 460n shown in FIG. 5F, and a full 2D image is generated through a collection of 1D image lines.

The advantage of scanning sub-aperture 460 instead of mechanically moving transducer 400 is that transducer 400 has remained stationary and is therefore registered with the image formed from scanning sub-aperture 460. The process of scanning sub-aperture 460 is repeated for various angular orientation of transducer 400 (transducer 400 is mechanically rotated in directions 415 and 416). Sub-aperture 460 in one embodiment is about 10 mm along its longest extent.

Once all of the imaging of tissue 14 has been completed a HIFU treatment may be planned by selecting various portions of tissue 14 for treatment. Controller 16, in one embodiment, automatically selects the portions of tissue 14 for treatment as described in U.S. Provisional Application No. 60/568,566 and the accompanying Appendix, which is expressly incorporated by reference herein. In another example, a user is presented with images of tissue 14 with display 512 and manually selects portions of tissue 14 for treatment with user input device 510.

Once the portions of tissue 14 have been selected for treatment, controller 16 selects a sub-aperture of transducer elements 402 provide HIFU therapy to a first portion of tissue 14, the first portion of tissue 14 having been selected for treatment, and determines the electronic delay and amplitude needed for the respective CWs of each selected transducer element to provide HIFU Therapy to the first portion of tissue 14. HIFU Therapy is provided to the first portion of tissue 14. Next controller 16 selects a second sub-aperture of transducer elements 402 to provide HIFU therapy to a second portion of tissue 14, the second portion of tissue 14 having been selected for treatment, and determines the electronic delay and amplitude needed for the respective CWs of each selected transducer element to provide HIFU Therapy to the second portion of tissue 14. HIFU Therapy is provided to the second portion of tissue 14. This procedure is repeated until all of the portions of tissue 14 which were selected for treatment have been treated with HIFU Therapy. As stated herein, it is possible to treat various portions of tissue 14 in parallel. Throughout the application of HIFU Therapy transducer 400 is not moved in longitudinal direction 114. Transducer 400 may be moved in rotational directions 115, 116. In one embodiment, after each application of HIFU Therapy, the respective portion of tissue 14 treated with that application of HIFU Therapy is imaged with a sub-aperture of transducer 400 to determine the effects of the HIFU Therapy.

Figure 7:
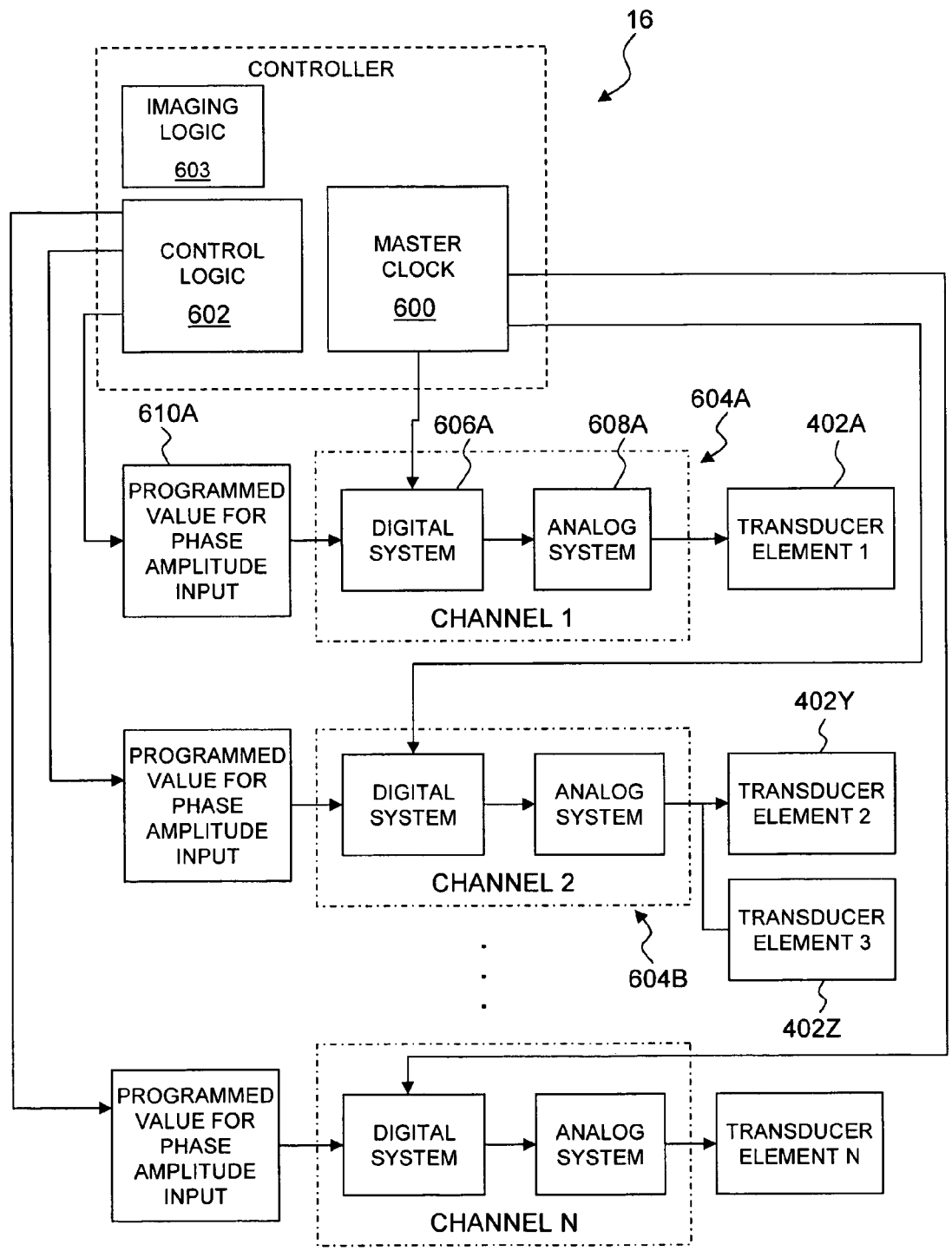
FIG. 7 is an exemplary embodiment of the controller of FIG. 6, the controller including a channel for each transducer element including a digital system and an analog system.
Figure 7A:
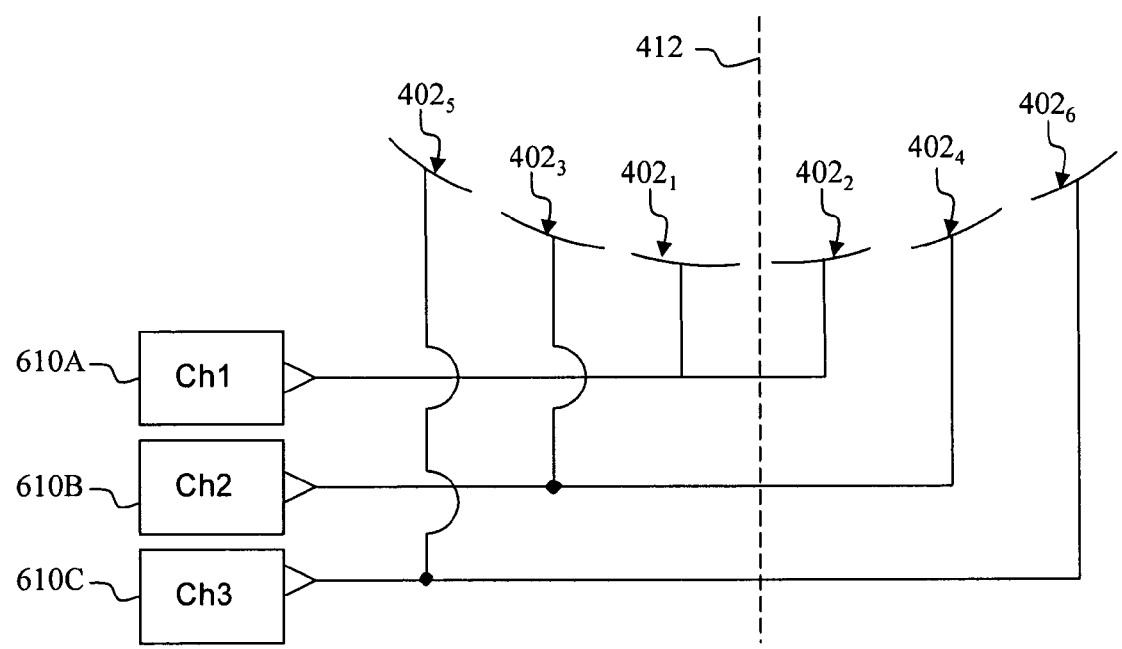
FIG. 7A is a illustration of multiple transducer elements being controlled by a single channel of FIG. 7.

Referring to FIG. 7, an exemplary embodiment of a portion of controller 16 is shown. Controller 16 includes a control logic 602, such as software to control HIFU System 500 and a master clock 600. The described portions of controller 16 in FIG. 7 are related to the therapy mode of HIFU System 500, the provision of HIFU Therapy to tissue 14. Controller 16 further includes imaging logic 603 which controls transducer 400 when HIFU System 500 is being used in an imaging mode, the generation of images of tissue 14. Control logic 602, in one embodiment, is software configured to determine which transducer elements are to be used in a sub-aperture to treat a given portion of tissue 14, the required phase delay for the CW generated by each transducer element within the sub-aperture to focus acoustic energy at the given portion of tissue 14 ("Phase input"), and the required amplitude of the CW generated by each transducer element within the sub-aperture to provide a therapeutic amount of acoustic power at the given portion of tissue 14 ("Amplitude input").

The emission of a CW for each transducer element 402 is controlled by electronics generally referred to as a channel 604. An exemplary channel 604A is described for transducer element 402A with the understanding that each transducer element 402 is controlled by a similar channel. Channel 604A includes a digital system 606A and an analog system 608A. Digital system 606A is programmed by controller 16 with Programmed Values for the Phase and Amplitude 610A such that analog system 608A drives transducer element 402A to emit a CW with the proper phase delay and the proper amplitude.

As shown in FIG. 7, controller 16 sends a reference clock signal from master clock 600 to each channel 604A. Master clock 600 provides a reference signal operating at a frequency of between about 500 kHz to about 6 MHz. In a preferred embodiment, master clock 600 provides a reference signal operating at a frequency of about 4 MHz. Controller 16 further configures each channel 604A by supplying the required Programmed Values for the Phase and Amplitude 610A for each channel 604A. In one embodiment, the reference signal provided by master clock 600 to each channel is a square wave signal. This square wave signal, as discussed herein, is delayed and/or pulse width modulated by each active channel 610 to provide a customized square wave signal to the associated analog electronics for each channel 610. The analog electronics, in turn, take this customized digital input and generate a respective sinusoidal driving signal to drive the respective transducer element(s), the sinusoidal driving signal having the appropriate phase delay and/or amplitude modulation for the respective transducer elements.

By digitally programming the phase information and the amplitude information for each channel 604, an otherwise complicated process, such as delaying an analog signal and/or modulating the amplitude of an analog signal, is greatly simplified. Further, digital system 606A is not as susceptible to cross-coupling as traditional analog electronics. In addition, the entire array 404 may be easily reprogrammed for a new focus or new intensity by simply changing one or more of the phase input or amplitude inputs to digital system 606.

Figure 8:
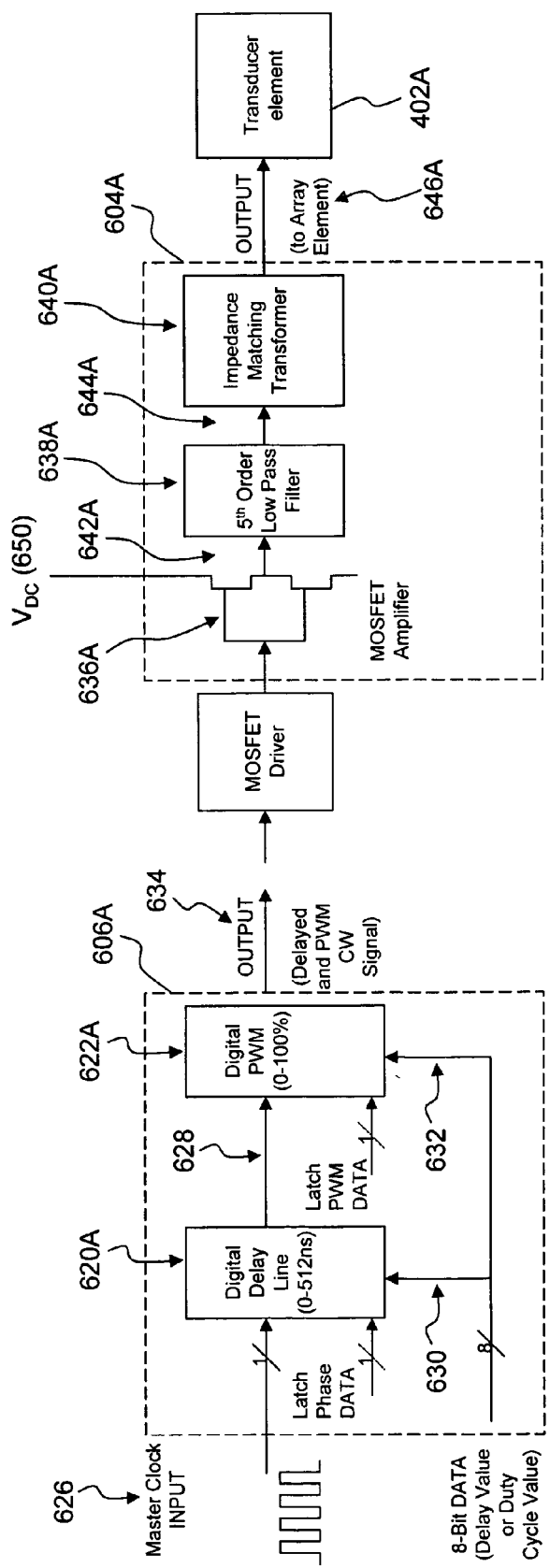
FIG. 8 is a exemplary embodiment of the digital system and the analog system of FIG. 7.

In a preferred embodiment of digital system 606A, shown in FIG. 8, a first integrated chip is programmed to operate as a delay line 620A and a second integrated chip is programmed to operate as a pulse width modulator 622A. In a preferred example, the integrated chip used for both delay line 620A and pulse width modulator 622A is a Model No. DS 1023-200 available from Dallas Semiconductor located at 4401 South Beltwood Parkway Dallas, Tex. 75244 USA. Delay line 620A receives the reference signal 626 from master clock 600 and has the capabilities to delay the phase of the respective channel, from 0 up to 360 degrees delay (one full cycle) to produce a delayed CW signal 628. The amount of delay is programmed into delay line 620A through an 8-bit write operation 630 from controller 16. Delayed CW signal 628 is then passed through pulse-width modulator 622A which controls the amplitude of each channel and has the capability to produce a signal, from 0% duty cycle (off, not in the sub-aperture) to 50% duty cycle (fully on, at full amplitude), to produce a Delayed and PWM CW 634. The percentage of the duty cycle is programmed into pulse width modulator 622A through an 8-bit write operation 632 from controller 16. As explained herein the amplitude of the final CW is produced by the analog electronics based on the pulse width modulation of the Delayed and PWM CW 634.

From the discussion above, it should be noted that each channel 604 may be digitally programmed by performed two 8-bit write operations. As such, each channel may be reprogrammed by simply sending two new 8-bit write operations to the respective channel. Thus, to fully program each channel 604 of a transducer, such as transducer 400, 2 8-bit write's are needed for each channel, accomplished via a simple and fast 8-bit digital interface to controller 16. Thus, to program a N-channel array, 2*N 8-bit write operations are needed.

In order to reduce the number of channels 604 required, multiple transducer elements 402 may be tied to the same channel 604, as represented by channel 604B in FIG. 7 wherein transducer elements 402Y and 402Z (see FIG. 4) are both tied to channel 604B. Transducer elements 402Y and 402Z may be tied together on channel 610B when transducer 400 is always intended to focus at locations located on plane 412 because transducer elements 402Y and 402Z mirror each other about plane 412.

In the preferred example, transducer 400 is about 80 mm in length and about 22 in width and includes about 826 elements arranged in six rows of 116, 138, 159, 159, 138, and 116 elements each. Further, in this example, face 401 is generally cylindrical along the rows of transducer elements 402, the cylinder having a radius of curvature of about 40 mm. Referring to FIG. 7B, in this example, for a given column 417, transducer elements 402 that mirror each other about plane 412 may be tied together. Illustratively transducer element pairs $402_1$ and $402_2$, $402_3$ and $402_4$, and $402_5$ and $402_6$ are tied together on channels 610A, 610B, and 610C, respectively. As such, only 413 channels are needed to control the 826 transducer elements as opposed to 826 separate channels.

In one embodiment, up to 64 channels may be located on a two board pair, one board for the digital systems 606 and one board for the analog systems 608. As such, additional transducer elements may be controlled by controller 16 simply through adding additional board pairs for digital system 606 and analog system 608. In one embodiment, controller 16 controls up to 1024 channels with digital systems 606 and analog system 608, each channel having up to 15 W output.

All boards may be set up to bypass individual functions. In one example, the integrated chip associated with pulse width modulator 622A is bypassed resulting in a system with phase control but without amplitude control using the same circuit board. In another example, by bypassing the amplifier components 636A on the analog board a system that only with filters is produced. In yet another embodiment, the impedance matching circuit 640A may be bypassed if it is not needed. The ability to bypass various components provides great flexibility. In another example, the overall acoustic amplitude of the transducer array is controlled by bypassing the pulse width modulator for each channel and simply varying the DC supply voltage 650 that powers the amplifiers.

The output of digital system 606A may be used to drive various analog electronics, examples discussed herein. In a preferred embodiment, the Delayed and PWM signal 634A is used to drive analog system 608A. Referring to FIG. 8, a preferred embodiment of analog system 608A is shown.

Delayed and PWM signal 634A is provided to analog system 608A which includes an amplifier 636A, a filter 638A, and an impedance matching transformer 640A. Delayed and PWM signal 634A is amplified by amplifier 636A. In one embodiment, amplifier 636A includes push-pull MOSFETS. Once amplified Delayed and PWM signal 634A is now a high-amplitude, positive and negative swing square wave (Amplified signal 642A). Amplified signal 642A is next filtered with filter 638A. In one embodiment, filter 638a is a low-pass filter which transforms the square wave of the amplified signal 642A into a high-amplitude, positive and negative swing sinusoidal wave, as required for driving the transducer element 402A. This signal is then impedance-matched to the array element 402 and cable with impedance matching transformer 640A.

In addition to transforming the square wave of the amplified signal 642A to a sinusoidal signal 644A, filter 648A adjusts the amplitude of the sinusoidal signal 644A. If low-pass filter 648A is presented with a square wave that is not 50% duty cycle, the output of filter 648A is a sinusoidal signal at a lower amplitude. Thus, when pulse width modulator 622A produces a delayed and PWM CW signal 634A having a duty cycle of less than 50%, filter 648A produces a sinusoidal signal having a reduced amplitude. In this manner by digitally controlling the pulse width of the delay and PWM CW signal 634A, the amplitude of the resultant CW driving transducer element 402A is controlled/reduced.

As stated above, digital system 606A may be used for several applications. For example, using only digital system 606A the delayed and PWM CW signal 634A is directly coupled to transducer element 402A. This will result in a system which is ideal for Schlieren or hydrophone characterization of beamshapes at low power. This example can be further varied by the inclusion of a low pass filter. This example can be further varied by the inclusion of a low pass filter and an impedance matching transformer. In another example, digital system 606A may be used with a low-power analog board. This example can be further varied by the inclusion of a low pass filter. This example can be further varied by the inclusion of a low pass filter and an impedance matching transformer. In yet another example, digital system 606A is used only with an amplifier. This example can be further varied by the inclusion of a low pass filter. This example can be further varied by the inclusion of a low pass filter and an impedance matching transformer.

Further details of suitable HIFU Systems which may be modified to execute the methods described herein are disclosed in U.S. Pat. No. 5,762,066; U.S. Pat. No. 5,117,832; U.S. Abandoned patent application Ser. No. 07/840,502 filed Feb. 21, 1992; U.S. Pat. No. 5,520,188; Australian Patent No. 5,732,801; Canadian Patent No. 1,332,441; Canadian Patent No. 2,250,081; U.S. Pat. No. 5,036,855; U.S. Pat. No. 5,492,126; U.S. Pat. No. 6,685,640; U.S. Provisional Patent Application No. 60/568,556, titled "Treatment of Spatially Oriented Disease with a Single Therapy, Imaging, and Doppler Ultrasound Transducer," each of which is expressly incorporated herein by reference.

Although the invention has been described in detail with reference to certain preferred embodiments, variations and modifications exist within the spirit and scope of the invention as described and defined in the following claims.

The invention claimed is:

1. A method of treating tissue with HIFU including a transducer, the method comprising the steps of:
   providing HIFU Therapy to a first portion of the tissue, the first portion being located at a first distance from the transducer;
   providing HIFU Therapy to a second portion of the tissue, the second portion being located at a second distance from the transducer, the second distance being further from the transducer than the first distance; and
   maintaining a generally constant f-number with the transducer when providing HIFU Therapy to both the first portion of the tissue and the second portion of the tissue, wherein the transducer includes an active surface having a plurality of transducer elements and wherein the step of maintaining the generally constant f-number comprises the steps of:
      selecting a first aperture of the active surface including a first number of the plurality of transducer elements for the provision of HIFU Therapy to the first portion of the tissue, the first number of transducer elements being configured to emit acoustic energy which will focus at the first distance from the transducer; and
      selecting a second aperture of the first active surface including a second number of the plurality of transducer elements for the provision of HIFU Therapy to the second portion of the tissue, the second number of transducer elements being configured to emit acoustic energy which will focus at the second distance from the transducer, wherein a ratio of the second distance to an active extent of the second aperture is generally equal to a ratio of the first distance to an active extent of the first aperture.

2. The method of claim 1, wherein the first portion of tissue and the second portion of tissue are located generally along an axis generally normal to a plane defined by a face of the transducer and further comprising the step of maintaining the transducer at a fixed location relative to the tissue for the provision of HIFU Therapy to each of the first portion of the tissue and the second portion of the tissue.

3. The method of claim 2, wherein the first number of transducer elements and the second number of transducer elements include at least one common transducer element of the plurality of transducer elements.

4. The method of claim 1, wherein the first portion of tissue is located along a first axis generally normal to a plane defined by a face of the transducer and the second portion of tissue is located along a second axis generally normal to the plane defined by the face of the transducer, the second axis being spaced apart from the first axis, and further comprising the step of maintaining the transducer at a fixed location relative to the tissue for the provision of HIFU Therapy to each of the first portion of the tissue and the second portion of the tissue.

5. The method of claim 4, wherein the first number of transducer elements are distinct from the second number of transducer elements.

6. The method of claim 1, wherein the first number of elements are centered relative to the first portion of the tissue and the second number of elements are centered relative to the second portion of the tissue.

7. A method of conducting a HIFU treatment to a target tissue, the method comprising the steps of:
   positioning a transducer proximate to target tissue, the transducer having a variable aperture;
   imaging the target tissue;
   selecting a plurality of treatment sites within the target tissue to be treated with HIFU Therapy, a first treatment site being located a first distance from the transducer and a second treatment site being located a second distance from the transducer, the second distance being further from the transducer than the first distance; and
   providing HIFU Therapy to the plurality of treatment sites with the transducer, the transducer having a first aperture when providing therapy to the second treatment site, at least one of an active extent of the first aperture and an active extent of the second aperture being chosen so that a ratio of the second distance to the active extent of the second aperture is generally equal to a ratio of the first distance to the active extent of the first aperture.

8. The method of claim 7, wherein the first treatment site and the second treatment site are located generally along an axis generally normal to a plane defined by a face of the transducer and further comprising the step of maintaining the transducer at a fixed location relative to the tissue for the provision of HIFU Therapy to each of the first treatment site and the second treatment site.

9. The method of claim 7, wherein the first treatment site is located along a first axis generally normal to a plane defined by a face of the transducer and the second treatment site is located along a second axis generally normal to the plane defined by the face of the transducer, the second axis being spaced apart from the first axis, and further comprising the step of maintaining the transducer at a fixed location relative to the tissue for the provision of HIFU Therapy to each of the first treatment site and the second treatment site.

10. A transducer for use with HIFU, the transducer, comprising:
   an active surface having a plurality of transducer elements; and
   a controller operably coupled to the transducer, the controller being configured to select which transducer elements emit acoustic energy and to control such emissions to focus the acoustic energy at various focal depths so that the active surface has a generally constant f-number at the various focal depths,
   wherein a first subset of the plurality of transducer elements are selected to define a first aperture of the active surface, the acoustic energy emitted from the first subset of the transducer elements being configured to focus at a first distance from the active surface and wherein a second subset of the transducer elements of the plurality of transducer elements are selected to define a second aperture of the active surface, the acoustic energy emitted from the second subset being configured to focus at a second distance from the active surface, the ratio of the first distance to an active extent of the first aperture being generally equal to the ratio of the second distance to an active extent of the second aperture.

11. The transducer of claim 10, wherein the controller configures each transducer element in the first subset of the transducer elements to emit a respective continuous acoustic wave, a phase of each respective acoustic wave being chosen to produce a constructive interference of the acoustic waves at the first distance.

12. The transducer of claim 11, wherein the continuous acoustic waves have a frequency of about 4 MHz and a duration of about 3 seconds.

13. The transducer of claim 10, wherein the ratio of the second distance to an active extent of the second aperture is about 1.0.

* * * * *